US012692228B2

(12) United States Patent
Mack et al.

(10) Patent No.: US 12,692,228 B2
(45) Date of Patent: Jul. 28, 2026

(54) METHOD FOR QUENCHING PEROXYCARBOXYLIC ACID RUNAWAY REACTIONS

(71) Applicant: ECOLAB USA INC., Saint Paul, MN (US)

(72) Inventors: David Andrew Mack, Saint Paul, MN (US); David D. McSherry, Saint Paul, MN (US); John W. Bolduc, Saint Paul, MN (US); Curtis Edward Finney, Saint Paul, MN (US); Corey Rosenthal, Saint Paul, MN (US); Junzhong Li, Saint Paul, MN (US)

(73) Assignee: ECOLAB USA INC., Saint Paul, MN (US)

(*) Notice: Subject to any disclaimer, the term of this patent is extended or adjusted under 35 U.S.C. 154(b) by 2 days.

(21) Appl. No.: 17/301,329

(22) Filed: Mar. 31, 2021

(65) Prior Publication Data

US 2021/0300839 A1 Sep. 30, 2021

Related U.S. Application Data

(60) Provisional application No. 63/002,434, filed on Mar. 31, 2020.

(51) Int. Cl.
*C07C 407/00* (2006.01)
*B01J 19/00* (2006.01)
(Continued)

(52) U.S. Cl.
CPC ......... *C07C 407/006* (2013.01); *B01J 19/002* (2013.01); *B65D 88/54* (2013.01);
(Continued)

(58) Field of Classification Search
CPC ... C07C 407/00; C07C 407/006; C07B 63/04; C01B 15/037; C01B 15/04;
(Continued)

(56) References Cited

U.S. PATENT DOCUMENTS

| | | | | |
|---|---|---|---|---|
| 2,347,434 A * | 4/1944 | Reichert | ............. | C07C 407/006 562/3 |
| 2,497,810 A * | 2/1950 | Campbell | ............. | C01B 15/032 423/586 |

(Continued)

FOREIGN PATENT DOCUMENTS

| | | |
|---|---|---|
| CA | 2016062 A1 | 11/1990 |
| CA | 2086003 A1 | 12/1991 |

(Continued)

OTHER PUBLICATIONS

Environmental Protection Agency ("How to prevent runaway reactions: case study: phenol-formaldehyde reaction hazards," Office of Solid Waste and Emergency Response, EPA 550-F99-004, 1999) (Year: 1999).*

(Continued)

*Primary Examiner* — Matthew R Diaz
(74) *Attorney, Agent, or Firm* — McKee, Voorhees & Sease, PLC

(57) ABSTRACT

Systems for quenching peroxycarboxylic acid and peroxide chemistry runaway reactions provide safe and efficacious systems to prevent uncontrolled runaway reactions, such as decomposition reactions, of peroxycarboxylic acid and peroxide chemistry compositions are disclosed. The systems provide prompt detection and dispensing of a stabilizer into a tank or other storage vessel containing a peroxide composition, peroxycarboxylic acid composition or a peroxycarboxylic acid-forming composition to stop a runaway
(Continued)

reaction. Methods for quenching peroxide and peroxycarboxylic acid runaway reactions are also disclosed.

7 Claims, 9 Drawing Sheets

(51) Int. Cl.
*B65D 88/54* (2006.01)
*B65D 90/22* (2006.01)
*C01B 15/037* (2006.01)
*C07B 63/04* (2006.01)

(52) U.S. Cl.
CPC ............ *B65D 90/22* (2013.01); *C01B 15/037* (2013.01); *C07B 63/04* (2013.01); *B01J 2219/00259* (2013.01); *B01J 2219/00272* (2013.01)

(58) Field of Classification Search
CPC .... C01B 15/055; B65D 88/54; B01J 19/0006; B01J 19/0013; B01J 19/002; B01J 2219/00245; B01J 2219/00259; B01J 2219/00272; B01J 2219/00637
See application file for complete search history.

(56) References Cited

U.S. PATENT DOCUMENTS 2,609,391 A 9/1952 Greenspan et al.
2,833,813 A 5/1958 Wallace
2,877,266 A 3/1959 Malcolm
2,955,905 A 10/1960 Davies et al.
3,048,624 A * 8/1962 Dunn .................. C07C 407/006 546/310
3,053,633 A * 9/1962 Dunlop ............... C07C 407/006 252/397
3,130,169 A 4/1964 Blumbergs et al.
3,156,654 A 11/1964 Konecny et al.
3,168,554 A 2/1965 Phillips et al.
3,192,254 A 6/1965 Hayes
3,256,198 A 6/1966 Matzner
3,272,750 A 9/1966 Chase
3,414,593 A 12/1968 Robson
3,432,546 A 3/1969 Oringer et al.
3,835,930 A * 9/1974 Denigan, Jr. .......... B65D 90/22 169/66
3,847,830 A 11/1974 Williams et al.
3,867,461 A * 2/1975 Leveskis ............. C07C 407/006 252/186.26
3,925,234 A 12/1975 Hachmann et al.
3,956,159 A 5/1976 Jones
3,969,258 A 7/1976 Carandang et al.
4,003,841 A 1/1977 Hachmann et al.
4,013,575 A 3/1977 Castrantas et al.
4,051,058 A * 9/1977 Bowing ............... C11D 3/3945 252/186.22
4,051,059 A 9/1977 Bowing et al.
4,100,095 A 7/1978 Hutchins et al.
4,126,573 A 11/1978 Johnston
4,129,517 A 12/1978 Eggensperger et al.
4,144,179 A 3/1979 Chatterji
4,170,453 A 10/1979 Kitko
4,233,235 A 11/1980 Camden et al.
4,259,201 A 3/1981 Cockrell, Jr. et al.
4,297,298 A 10/1981 Crommelynck et al.
4,311,598 A 1/1982 Verachtert
4,367,156 A 1/1983 Diehl
4,370,251 A 1/1983 Liao et al.
4,374,035 A 2/1983 Bossu
4,391,723 A 7/1983 Bacon et al.
4,391,724 A 7/1983 Bacon
4,412,934 A 11/1983 Chung et al.
4,430,236 A 2/1984 Franks
4,470,919 A 9/1984 Goffinet et al.
4,473,507 A 9/1984 Bossu
4,483,778 A 11/1984 Thompson et al.
4,486,327 A 12/1984 Murphy et al.
4,529,534 A 7/1985 Richardson
4,540,721 A 9/1985 Staller
4,561,999 A 12/1985 Sekiguchi et al.
4,563,112 A 1/1986 Mokuya et al.
4,587,264 A 5/1986 Jourdan-Laforte et al.
4,588,506 A 5/1986 Raymond et al.
4,595,520 A 6/1986 Heile et al.
4,617,090 A 10/1986 Chum et al.
4,655,781 A 4/1987 Hsieh et al.
4,661,280 A 4/1987 Ouhadi et al.
4,681,592 A 7/1987 Hardy et al.
4,743,447 A 5/1988 Le Rouzic et al.
4,744,916 A 5/1988 Adams et al.
4,769,168 A 9/1988 Ouhadi et al.
4,778,618 A 10/1988 Fong et al.
4,783,278 A 11/1988 Sanderson et al.
4,786,431 A 11/1988 Broze et al.
4,797,225 A 1/1989 Broze et al.
4,820,440 A 4/1989 Hemm et al.
4,846,992 A 7/1989 Fonsny et al.
4,853,143 A 8/1989 Hardy et al.
4,879,057 A 11/1989 Dankowski et al.
4,917,815 A 4/1990 Beilfuss et al.
4,957,647 A 9/1990 Zielske
4,964,870 A 10/1990 Fong et al.
5,004,558 A 4/1991 Dyroff et al.
5,019,292 A 5/1991 Baeck et al.
5,030,240 A 7/1991 Wiersema et al.
5,073,285 A 12/1991 Liberati et al.
5,098,598 A 3/1992 Sankey et al.
5,117,049 A 5/1992 Venturello et al.
5,132,036 A 7/1992 Falou et al.
5,139,788 A 8/1992 Schmidt
5,143,641 A 9/1992 Nunn
5,157,087 A * 10/1992 Hogt ..................... C07C 409/16 525/391
5,160,656 A 11/1992 Carron et al.
5,196,133 A 3/1993 Leslie et al.
5,200,189 A 4/1993 Oakes et al.
5,246,620 A 9/1993 Gethoeffer et al.
5,250,212 A 10/1993 de Buzzaccarini et al.
5,250,707 A 10/1993 Inaba et al.
5,264,229 A 11/1993 Mannig et al.
5,266,587 A 11/1993 Sankey et al.
5,268,003 A 12/1993 Coope et al.
5,274,369 A 12/1993 Tsunoda et al.
5,281,351 A 1/1994 Romeo et al.
5,288,746 A 2/1994 Pramod
5,296,239 A 3/1994 Colery et al.
5,310,774 A 5/1994 Farrar
5,314,687 A 5/1994 Oakes et al.
5,320,821 A * 6/1994 Nagashima ........... C01B 15/029 423/584
5,340,501 A 8/1994 Steindorf
5,344,652 A 9/1994 Hall, II et al.
5,349,083 A 9/1994 Brougham et al.
5,362,899 A 11/1994 Campbell
5,374,369 A 12/1994 Angevaare et al.
5,382,571 A 1/1995 Granger et al.
5,383,977 A 1/1995 Pearce
5,391,324 A 2/1995 Reinhardt et al.
5,398,506 A 3/1995 Martin
5,409,629 A 4/1995 Shulman et al.
5,409,713 A 4/1995 Lokkesmoe et al.
5,415,807 A 5/1995 Gosselink et al.
5,422,028 A 6/1995 Oakes et al.
5,431,848 A 7/1995 Getty
5,431,849 A 7/1995 Damhus et al.
5,433,881 A 7/1995 Townend et al.
5,435,808 A 7/1995 Holzhauer et al.
5,437,686 A 8/1995 Heffner et al.
5,447,648 A 9/1995 Steindorf
5,453,214 A 9/1995 van den Berg et al.
5,454,563 A 10/1995 Nagamoto et al.
5,463,112 A 10/1995 Sankey et al.

(56) References Cited

U.S. PATENT DOCUMENTS

| | | | | |
|---|---|---|---|---|
| 5,464,563 | A | | 11/1995 | Moore et al. |
| 5,466,825 | A | | 11/1995 | Carr et al. |
| 5,472,619 | A | | 12/1995 | Holzhauer et al. |
| 5,475,123 | A | | 12/1995 | Bos |
| 5,486,212 | A | | 1/1996 | Mitchell et al. |
| 5,496,728 | A | | 3/1996 | Hardy et al. |
| 5,503,765 | A | | 4/1996 | Schepers et al. |
| 5,505,740 | A | | 4/1996 | Kong et al. |
| 5,525,121 | A | | 6/1996 | Heffner et al. |
| 5,545,374 | A | | 8/1996 | French et al. |
| 5,565,231 | A | | 10/1996 | Malone et al. |
| 5,576,282 | A | | 11/1996 | Miracle et al. |
| 5,578,134 | A | | 11/1996 | Lentsch et al. |
| 5,589,507 | A | | 12/1996 | Il et al. |
| 5,595,967 | A | | 1/1997 | Miracle et al. |
| 5,599,781 | A | | 2/1997 | Haeggberg et al. |
| 5,616,281 | A | | 4/1997 | Hardy et al. |
| 5,617,710 | A | | 4/1997 | Goossens et al. |
| 5,624,634 | A | | 4/1997 | Brougham et al. |
| 5,632,676 | A | | 5/1997 | Kurschner et al. |
| 5,635,195 | A | | 6/1997 | Hall, II et al. |
| 5,637,755 | A | | 6/1997 | Nagumo et al. |
| 5,647,997 | A | | 7/1997 | Holzhauer et al. |
| 5,654,464 | A | * | 8/1997 | Abma ................ C07C 407/006 558/264 |
| 5,672,739 | A | | 9/1997 | Varadaraj et al. |
| 5,681,805 | A | | 10/1997 | Scheuing et al. |
| 5,683,724 | A | | 11/1997 | Hei et al. |
| 5,683,977 | A | | 11/1997 | Jureller et al. |
| 5,691,298 | A | | 11/1997 | Gosselink et al. |
| 5,698,506 | A | | 12/1997 | Angevaare et al. |
| 5,716,923 | A | | 2/1998 | MacBeath |
| 5,718,910 | A | | 2/1998 | Oakes et al. |
| 5,755,977 | A | | 5/1998 | Gurol et al. |
| 5,767,308 | A | | 6/1998 | Thiele et al. |
| 5,780,064 | A | | 7/1998 | Meisters et al. |
| 5,785,867 | A | | 7/1998 | Lazonby et al. |
| 5,814,592 | A | | 9/1998 | Kahn et al. |
| 5,817,614 | A | | 10/1998 | Miracle et al. |
| 5,827,447 | A | | 10/1998 | Tamura et al. |
| 5,827,808 | A | | 10/1998 | Appleby et al. |
| 5,840,343 | A | | 11/1998 | Hall, II et al. |
| 5,872,092 | A | | 2/1999 | Kong-Chan et al. |
| 5,880,083 | A | | 3/1999 | Beaujean et al. |
| 5,886,216 | A | * | 3/1999 | Pudas .................. C07C 407/00 562/2 |
| 5,900,187 | A | | 5/1999 | Scialla et al. |
| 5,900,256 | A | | 5/1999 | Scoville, Jr. et al. |
| 5,914,303 | A | | 6/1999 | Sankey et al. |
| 5,928,382 | A | | 7/1999 | Reinhardt et al. |
| 5,929,012 | A | | 7/1999 | Del Duca et al. |
| 5,965,033 | A | | 10/1999 | Huss et al. |
| 5,965,785 | A | | 10/1999 | Braden et al. |
| 5,968,885 | A | | 10/1999 | Del Duca et al. |
| 5,968,893 | A | | 10/1999 | Manohar et al. |
| 5,977,403 | A | | 11/1999 | Byers |
| 5,998,350 | A | | 12/1999 | Burns et al. |
| 6,004,922 | A | | 12/1999 | Watson et al. |
| 6,008,405 | A | * | 12/1999 | Gray .................. C07C 407/006 562/3 |
| 6,010,729 | A | | 1/2000 | Gutzmann et al. |
| 6,014,536 | A | | 1/2000 | Ban et al. |
| 6,022,381 | A | | 2/2000 | Dias et al. |
| 6,024,986 | A | | 2/2000 | Hei |
| 6,049,002 | A | | 4/2000 | Mattila et al. |
| 6,080,712 | A | * | 6/2000 | Revell ................. C11D 3/3945 252/186.26 |
| 6,103,286 | A | | 8/2000 | Gutzmann et al. |
| 6,110,883 | A | | 8/2000 | Petri et al. |
| 6,136,769 | A | | 10/2000 | Asano et al. |
| 6,156,129 | A | | 12/2000 | Hlivka et al. |
| 6,156,156 | A | | 12/2000 | Rousu et al. |
| 6,165,483 | A | | 12/2000 | Hei et al. |
| 6,177,393 | B1 | | 1/2001 | McGregor et al. |
| 6,183,763 | B1 | | 2/2001 | Beerse et al. |
| 6,183,807 | B1 | | 2/2001 | Gutzmann et al. |
| 6,196,719 | B1 | | 3/2001 | Brown |
| 6,201,110 | B1 | | 3/2001 | Olsen et al. |
| 6,207,632 | B1 | | 3/2001 | Brooker et al. |
| 6,211,237 | B1 | | 4/2001 | Huss et al. |
| 6,218,429 | B1 | | 4/2001 | Ohkawa et al. |
| 6,221,341 | B1 | | 4/2001 | Montgomery |
| 6,238,685 | B1 | | 5/2001 | Hei et al. |
| 6,257,253 | B1 | | 7/2001 | Lentsch et al. |
| 6,262,013 | B1 | | 7/2001 | Smith et al. |
| 6,274,542 | B1 | | 8/2001 | Carr et al. |
| 6,277,804 | B1 | | 8/2001 | Kahn et al. |
| 6,284,793 | B1 | | 9/2001 | Fuchs et al. |
| 6,294,186 | B1 | | 9/2001 | Beerse et al. |
| 6,310,025 | B1 | | 10/2001 | Del Duca et al. |
| 6,326,032 | B1 | | 12/2001 | Richter et al. |
| 6,346,279 | B1 | | 2/2002 | Rochon |
| 6,379,711 | B1 | * | 4/2002 | Frenkel ................. C01B 15/037 252/186.28 |
| 6,384,008 | B1 | | 5/2002 | Parry |
| 6,399,564 | B1 | | 6/2002 | Speed et al. |
| 6,407,052 | B2 | | 6/2002 | Gassenmeier et al. |
| 6,417,151 | B1 | | 7/2002 | Grothus et al. |
| 6,432,661 | B1 | | 8/2002 | Heitfeld et al. |
| 6,436,885 | B2 | | 8/2002 | Biedermann et al. |
| 6,444,634 | B1 | | 9/2002 | Mason et al. |
| 6,468,472 | B1 | | 10/2002 | Yu et al. |
| 6,503,876 | B1 | | 1/2003 | Broeckx |
| 6,517,057 | B1 | * | 2/2003 | Aichinger .............. B01J 19/002 261/77 |
| 6,528,471 | B1 | | 3/2003 | Del Duca et al. |
| 6,537,958 | B1 | | 3/2003 | Di Capua et al. |
| 6,545,047 | B2 | | 4/2003 | Gutzmann et al. |
| 6,548,467 | B2 | | 4/2003 | Baker et al. |
| 6,548,470 | B1 | | 4/2003 | De Buzzaccarini et al. |
| 6,566,318 | B2 | | 5/2003 | Perkins et al. |
| 6,569,286 | B1 | | 5/2003 | Withenshaw et al. |
| 6,576,602 | B1 | | 6/2003 | Smerznak et al. |
| 6,589,565 | B1 | | 7/2003 | Richter et al. |
| 6,599,871 | B2 | | 7/2003 | Smith |
| 6,602,845 | B2 | | 8/2003 | Connor et al. |
| 6,607,710 | B1 | | 8/2003 | Ito et al. |
| 6,627,593 | B2 | | 9/2003 | Hei et al. |
| 6,627,594 | B1 | | 9/2003 | James et al. |
| 6,627,657 | B1 | | 9/2003 | Hilgren et al. |
| 6,635,286 | B2 | | 10/2003 | Hei et al. |
| 6,649,140 | B2 | | 11/2003 | Paparatto et al. |
| 6,660,707 | B2 | | 12/2003 | Lentsch et al. |
| 6,677,477 | B2 | * | 1/2004 | Pohjanvesi ......... C07C 407/006 562/6 |
| 6,686,324 | B2 | | 2/2004 | Ramirez |
| 6,689,732 | B1 | | 2/2004 | Guedira et al. |
| 6,693,069 | B2 | | 2/2004 | Koerber et al. |
| 6,696,093 | B2 | | 2/2004 | Ney et al. |
| 6,699,828 | B1 | | 3/2004 | De Buzzaccarini et al. |
| 6,770,774 | B2 | | 8/2004 | Van De Bovenkamp-Bouwman et al. |
| 6,803,057 | B2 | | 10/2004 | Ramirez et al. |
| 6,806,246 | B2 | | 10/2004 | Preissner et al. |
| 6,830,591 | B1 | | 12/2004 | Wang et al. |
| 6,841,090 | B1 | | 1/2005 | Serego et al. |
| 6,866,749 | B2 | | 3/2005 | Delmas et al. |
| 6,878,680 | B2 | | 4/2005 | Kitko et al. |
| 6,899,452 | B2 | * | 5/2005 | Hamamoto ............ B01J 19/002 366/152.2 |
| 6,919,304 | B2 | | 7/2005 | Dykstra et al. |
| 7,012,053 | B1 | | 3/2006 | Barnabas et al. |
| 7,012,154 | B2 | | 3/2006 | Vineyard et al. |
| 7,060,136 | B1 | | 6/2006 | Zeiher et al. |
| 7,078,373 | B2 | | 7/2006 | Burrows et al. |
| 7,148,351 | B2 | | 12/2006 | Morris et al. |
| 7,169,236 | B2 | | 1/2007 | Zeiher et al. |
| 7,189,385 | B2 | | 3/2007 | Montgomery |
| 7,217,295 | B2 | | 5/2007 | Samain et al. |
| 7,243,664 | B2 | | 7/2007 | Berger et al. |
| 7,431,775 | B2 | | 10/2008 | Wang et al. |
| 7,448,255 | B2 | | 11/2008 | Hoots et al. |
| 7,494,963 | B2 | | 2/2009 | Ahmed et al. |
| 7,498,051 | B2 | | 3/2009 | Man et al. |

(56) References Cited

U.S. PATENT DOCUMENTS 7,524,803 B2 4/2009 Lentsch et al.
7,541,324 B2 6/2009 Reinhardt et al.
7,569,232 B2 8/2009 Man et al.
7,569,528 B2 8/2009 Lant et al.
7,598,218 B2 10/2009 Stolte et al.
7,601,789 B2 10/2009 Morris et al.
7,618,545 B2 11/2009 Wakao et al.
7,682,403 B2 3/2010 Gohl et al.
7,686,892 B2 3/2010 Smets et al.
7,723,083 B2 5/2010 DiCosimo et al.
7,771,737 B2 8/2010 Man et al.
7,863,234 B2 1/2011 Maki et al.
7,875,720 B2 1/2011 Morris et al.
7,887,641 B2 2/2011 Man et al.
7,910,371 B2 3/2011 Johnson
7,915,445 B2 3/2011 Maatta et al.
7,919,122 B2 4/2011 Okano et al.
7,922,828 B2 4/2011 Smith et al.
7,949,432 B2 5/2011 Rice
7,981,679 B2 7/2011 Rice
7,985,318 B2 7/2011 Shevchenko et al.
8,017,409 B2 9/2011 Tokhtuev et al.
8,030,351 B2 10/2011 Gutzmann et al.
8,071,528 B2 12/2011 Smith et al.
8,080,404 B1 12/2011 Turetsky et al.
8,084,756 B2 12/2011 Tokhtuev et al.
8,110,603 B2 2/2012 Kawabata et al.
8,119,412 B2 2/2012 Kraus
8,153,573 B2 4/2012 Miralles et al.
8,178,336 B2 5/2012 Derkx et al.
8,226,939 B2 7/2012 Herdt et al.
8,231,917 B2 7/2012 Herdt et al.
8,236,573 B2 8/2012 Tokhtuev et al.
8,241,624 B2 8/2012 Herdt et al.
8,309,507 B2 11/2012 Fernandez Prieto et al.
8,344,026 B2 1/2013 Li et al.
8,426,634 B2 4/2013 Neas et al.
8,729,296 B2 5/2014 Fast et al.
8,822,719 B1 9/2014 Li et al.
8,828,910 B2* 9/2014 Aksela .................. C07C 407/00 504/160
8,933,263 B2* 1/2015 Herdt ................... B01J 19/0006 562/6
9,005,669 B2 4/2015 Allen et al.
9,012,504 B2 4/2015 Olson et al.
9,034,390 B2 5/2015 Kielbania
9,169,044 B2* 10/2015 Eckholm, II ........... B65D 90/22
9,288,992 B2 3/2016 Li et al.
9,321,664 B2 4/2016 Li et al.
9,585,397 B2 3/2017 Li et al.
9,630,847 B2* 4/2017 McNeel ............... B01J 19/0013
9,676,711 B2 6/2017 Junzhong et al.
9,701,931 B2 7/2017 Moore
9,708,256 B2* 7/2017 McSherry ............. C07C 407/00
9,752,105 B2 9/2017 Stokes et al.
9,902,627 B2 2/2018 Li et al.
9,957,202 B2* 5/2018 Martin .................... C07B 63/04
10,165,774 B2 1/2019 Li et al.
10,893,674 B2 1/2021 Li et al.
11,026,421 B2 6/2021 Li et al.
2001/0054201 A1 12/2001 Wang et al.
2002/0007516 A1 1/2002 Wang
2002/0040151 A1 4/2002 Fontenot et al.
2002/0055043 A1 5/2002 Morikawa et al.
2002/0064565 A1 5/2002 Karagoezian
2002/0086903 A1 7/2002 Giambrone et al.
2002/0102702 A1 8/2002 Osten et al.
2002/0128312 A1 9/2002 Hei et al.
2002/0157189 A1 10/2002 Wang et al.
2002/0160928 A1 10/2002 Smerznak et al.
2002/0161258 A1 10/2002 Miracle et al.
2002/0169088 A1 11/2002 Wang
2002/0188026 A1 12/2002 Singh et al.
2002/0193626 A1 12/2002 Pohjanvesi et al.
2003/0012681 A1 1/2003 Yeganeh et al.
2003/0045443 A1 3/2003 Korber et al.
2003/0100468 A1 5/2003 Smerznak et al.
2003/0100469 A1 5/2003 Connor et al.
2003/0119699 A1 6/2003 Miracle et al.
2003/0148909 A1 8/2003 Del Duca et al.
2003/0154556 A1 8/2003 Del Duca et al.
2003/0180377 A1 9/2003 Ramirez et al.
2003/0234382 A1 12/2003 Sato et al.
2003/0235623 A1 12/2003 Van Oosterom
2004/0002616 A1 1/2004 Preto et al.
2004/0010858 A1 1/2004 Detering et al.
2004/0016060 A1 1/2004 Detering et al.
2004/0025262 A1 2/2004 Hamers et al.
2004/0033269 A1 2/2004 Hei et al.
2004/0035537 A1 2/2004 Delmas et al.
2004/0072718 A1 4/2004 Price et al.
2004/0077514 A1 4/2004 Price et al.
2004/0107506 A1 6/2004 Detering et al.
2004/0112439 A1* 6/2004 Eisenhut ................ B65D 90/22 137/576
2004/0139559 A1 7/2004 Detering et al.
2004/0266653 A1 12/2004 Delplancke et al.
2005/0000908 A1 1/2005 Karlsson et al.
2005/0008526 A1 1/2005 Bianchetti et al.
2005/0126282 A1* 6/2005 Maatuk ................. G01F 23/246 73/295
2005/0146305 A1 7/2005 Kneller
2005/0222003 A1 10/2005 Gagliardi et al.
2005/0226800 A1 10/2005 Wang et al.
2005/0241817 A1 11/2005 Moore et al.
2005/0281773 A1 12/2005 Wieland et al.
2005/0288204 A1 12/2005 Matts et al.
2006/0040847 A1 2/2006 Weibel
2006/0043340 A1 3/2006 Koizumi et al.
2006/0065469 A1 3/2006 Stefano et al.
2006/0088498 A1 4/2006 Martin et al.
2006/0172909 A1 8/2006 Schmiedel et al.
2006/0173209 A1 8/2006 Vineyard et al.
2006/0199742 A1 9/2006 Arisz et al.
2006/0247151 A1 11/2006 Kaaret et al.
2006/0254001 A1 11/2006 Hoeffkes et al.
2006/0257964 A1 11/2006 Larose
2006/0276366 A1 12/2006 Deljosevic et al.
2006/0289364 A1 12/2006 Wakao et al.
2007/0010420 A1 1/2007 Lange et al.
2007/0042924 A1 2/2007 DiCosimo et al.
2007/0087954 A1 4/2007 Wang et al.
2007/0093407 A1 4/2007 Bianchetti et al.
2007/0102359 A1 5/2007 Lombardi et al.
2007/0105744 A1 5/2007 Amiconi et al.
2007/0113875 A1 5/2007 Wang et al.
2007/0163779 A1 7/2007 Rae et al.
2007/0173430 A1 7/2007 Souter et al.
2007/0225197 A1 9/2007 Kruse et al.
2007/0281002 A1 12/2007 Morales et al.
2008/0001125 A1 1/2008 Zetlmeisl et al.
2008/0064619 A1 3/2008 Bastigkeit et al.
2008/0095677 A1 4/2008 McSherry et al.
2008/0095861 A1 4/2008 Walker
2008/0146482 A1 6/2008 Schneiderman et al.
2008/0176784 A1 7/2008 Clowes et al.
2008/0194449 A1 8/2008 Becker et al.
2008/0200364 A1 8/2008 Garaffa et al.
2008/0312107 A1 12/2008 Harris et al.
2009/0005286 A1 1/2009 Detering et al.
2009/0011971 A1 1/2009 Evers
2009/0018049 A1 1/2009 Stolte et al.
2009/0043123 A1 2/2009 Copenhafer et al.
2009/0047176 A1 2/2009 Cregger et al.
2009/0061017 A1 3/2009 Pedersen et al.
2009/0075856 A1 3/2009 Schmiedel et al.
2009/0088347 A1 4/2009 Mukhopadhyay et al.
2009/0145202 A1 6/2009 Tokhtuev et al.
2009/0148686 A1 6/2009 Urankar et al.
2009/0175956 A1 7/2009 Buschmann et al.
2009/0188055 A1 7/2009 Bernhardt et al.
2009/0221704 A1 9/2009 Aksela et al.
2009/0249557 A1 10/2009 Maki et al.
2009/0263904 A1 10/2009 Clinton et al.

(56) References Cited

U.S. PATENT DOCUMENTS

2009/0269324 A1 10/2009 Herdt et al.
2009/0294382 A1 12/2009 Fukuyo et al.
2010/0002115 A1 1/2010 Liu
2010/0021557 A1 1/2010 Li et al.
2010/0021558 A1 1/2010 Dada et al.
2010/0041579 A1 2/2010 Bianchetti et al.
2010/0041752 A1 2/2010 Dicosimo et al.
2010/0048730 A1 2/2010 Li et al.
2010/0084603 A1 4/2010 Narayan et al.
2010/0108566 A1 5/2010 Scattergood et al.
2010/0140186 A1 6/2010 Huang et al.
2010/0143491 A1 6/2010 Kawabata et al.
2010/0160449 A1 6/2010 Rovison et al.
2010/0222242 A1 9/2010 Huang et al.
2010/0227000 A1 9/2010 Board et al.
2010/0227829 A1 9/2010 Licari et al.
2010/0275382 A1 11/2010 Calvert
2010/0286017 A1 11/2010 Righetto
2010/0308260 A1 12/2010 Maki et al.
2011/0052445 A1 3/2011 Herdt et al.
2011/0082324 A1* 4/2011 Wellenhofer ............ B01J 8/001 585/501
2011/0146707 A1 6/2011 Cermenati et al.
2011/0168567 A1 7/2011 Smith et al.
2011/0169270 A1 7/2011 Todorof
2011/0171062 A1 7/2011 Wolfe
2011/0173897 A1 7/2011 Schneider
2011/0177145 A1 7/2011 Erkenbrecher, Jr. et al.
2011/0217761 A1 9/2011 Hilgren et al.
2011/0226293 A1 9/2011 Bonnechere et al.
2011/0230380 A1 9/2011 Holzhauer et al.
2011/0240510 A1 10/2011 De Poortere et al.
2011/0257060 A1 10/2011 Dykstra
2011/0274974 A1 11/2011 Sabi et al.
2011/0311645 A1 12/2011 Diaz
2012/0012307 A1 1/2012 Nevin
2012/0024525 A1 2/2012 Svarczkopf et al.
2012/0052134 A1 3/2012 Li et al.
2012/0070339 A1 3/2012 Lawal
2012/0085236 A1 4/2012 McCorriston et al.
2012/0085931 A1 4/2012 Burns et al.
2012/0097614 A1 4/2012 Silva et al.
2012/0149121 A1 6/2012 Tokhtuev et al.
2012/0164236 A1 6/2012 Iwasa et al.
2012/0172440 A1 7/2012 Li et al.
2012/0172441 A1 7/2012 Li et al.
2012/0225943 A1 9/2012 Gohl et al.
2012/0321510 A1 12/2012 Herdt et al.
2013/0018097 A1 1/2013 Bolduc et al.
2013/0022496 A1 1/2013 Herdt et al.
2013/0053512 A1 2/2013 Kojima et al.
2013/0063512 A1 3/2013 Takagi et al.
2013/0143786 A1 6/2013 Zhu et al.
2013/0210923 A1 8/2013 Zhu
2013/0247308 A1 9/2013 Duerrschmidt et al.
2013/0344556 A1* 12/2013 Fernholz ................ A01N 25/02 435/252.1
2014/0096971 A1 4/2014 Keizer et al.
2014/0097144 A1* 4/2014 Li ............................ C02F 1/40 210/759
2014/0120179 A1 5/2014 Smith et al.
2014/0121272 A1 5/2014 Smith et al.
2014/0255514 A1 9/2014 Li et al.
2014/0256811 A1* 9/2014 Li .......................... A01N 25/22 514/558
2014/0335199 A1 11/2014 Li et al.
2016/0150779 A1 6/2016 Li et al.
2016/0176814 A1 6/2016 Balasubramanian et al.
2016/0176815 A1 6/2016 Li et al.
2016/0200595 A1 7/2016 Li et al.
2016/0205946 A1 7/2016 Stauffer et al.
2016/0348037 A1 12/2016 Findlay et al.
2017/0020130 A1 1/2017 Buschmann et al.
2017/0064949 A1 3/2017 Kraus et al.
2017/0118989 A1 5/2017 Oppong et al.
2017/0245499 A1 8/2017 Fast et al.
2018/0042231 A1 2/2018 Del Negro et al.
2018/0187129 A1 7/2018 Traistaru et al.
2019/0016678 A1 1/2019 Ganguly-Mink et al.
2019/0069547 A1 3/2019 Kraus et al.
2019/0092661 A1* 3/2019 Fast ....................... A01N 25/02
2019/0208780 A1 7/2019 McSherry et al.
2019/0225510 A1 7/2019 Li et al.
2020/0060265 A1* 2/2020 Nagel .................. C11D 7/3281
2020/0290873 A1* 9/2020 Yokoi ................. C01B 15/0135
2020/0306401 A1 10/2020 Cookson et al.
2020/0323205 A1 10/2020 Kraus et al.
2021/0015096 A1 1/2021 Herdt et al.
2021/0029996 A1 2/2021 Li et al.

FOREIGN PATENT DOCUMENTS

CA 1300465 C 5/1992
CA 1305721 C 7/1992
CA 2325709 A1 5/2001
CN 1751768 A 3/2006
CN 100486668 C 5/2009
CN 101314632 B 12/2010
CN 112479963 A * 3/2021 ......... C07C 407/006
DE 1024514 B 2/1958
DE 2451904 A1 5/1975
DE 2616049 A1 10/1977
DE 19754290 A1 6/1999
DE 19853845 A1 5/2000
DE 10011273 A1 9/2001
EP 0061393 A1 9/1982
EP 0068547 A1 1/1983
EP 0075419 A2 3/1983
EP 0231632 A2 8/1987
EP 267175 A2 5/1988
EP 0273775 A2 7/1988
EP 334427 A1 9/1989
EP 0349220 A2 1/1990
EP 0384911 A2 8/1990
EP 0387049 A2 9/1990
EP 0396341 A2 11/1990
EP 0415028 A1 3/1991
EP 0280697 B1 9/1992
EP 0557419 A1 9/1993
EP 626371 A1 * 11/1994 ............. A01N 37/16
EP 0442549 B1 10/1996
EP 0741776 B1 11/1996
EP 0751210 A1 1/1997
EP 0822183 A2 2/1998
EP 0845526 A2 6/1998
EP 0906950 A1 4/1999
EP 1001012 A1 5/2000
EP 1114137 A1 7/2001
EP 1129171 A1 9/2001
EP 1717302 A1 11/2006
EP 2271410 A2 1/2011
EP 2329893 A1 6/2011
EP 2522714 A1 11/2012
EP 2522715 A1 11/2012
EP 2714877 A1 4/2014
EP 2566943 B1 9/2017
GB 1198734 A 7/1970
GB 1584170 A 2/1981
GB 2179364 A 3/1987
GB 2179365 A 3/1987
GB 2187199 A 9/1987
GB 2195124 A 3/1988
GB 2195125 A 3/1988
GB 2195649 A 4/1988
GB 2208233 A 3/1989
GB 2279660 A 1/1995
GB 2281744 A 3/1995
GB 2361687 A 10/2001
JP S62155203 A 7/1987
JP H05140079 A 6/1993
JP H05186989 A 7/1993
JP 06340617 A * 12/1994 ......... C07C 407/006
JP H0892594 A 4/1996
JP H0892595 A 4/1996

(56) References Cited

FOREIGN PATENT DOCUMENTS

| | | | | | |
|---|---|---|---|---|---|
| JP | H08143898 | A | | 6/1996 | |
| JP | H08245549 | A | | 9/1996 | |
| JP | 2000357633 | A | | 12/2000 | |
| JP | 2002105352 | A | | 4/2002 | |
| JP | 2006045146 | A | | 2/2006 | |
| JP | 2006045147 | A | | 2/2006 | |
| JP | 2007084589 | A | | 4/2007 | |
| JP | 2008092594 | A | | 4/2008 | |
| JP | 2008245549 | A | | 10/2008 | |
| KR | 20060007497 | A | | 1/2006 | |
| WO | 9007501 | A1 | | 7/1990 | |
| WO | 9106574 | A1 | | 5/1991 | |
| WO | WO-91/07375 | A1 | * | 5/1991 | ......... C07C 407/006 |
| WO | 9114674 | A1 | | 10/1991 | |
| WO | 9115474 | A1 | | 10/1991 | |
| WO | 9208471 | A1 | | 5/1992 | |
| WO | 9403395 | A1 | | 2/1994 | |
| WO | 9403580 | A1 | | 2/1994 | |
| WO | 9410284 | A1 | | 5/1994 | |
| WO | 9413776 | A1 | | 6/1994 | |
| WO | 9418299 | A1 | | 8/1994 | |
| WO | 9419446 | A1 | | 9/1994 | |
| WO | 1994020600 | A1 | | 9/1994 | |
| WO | 9424869 | A1 | | 11/1994 | |
| WO | 9429509 | A1 | | 12/1994 | |
| WO | 9502030 | A1 | | 1/1995 | |
| WO | 9504128 | A1 | | 2/1995 | |
| WO | 9521122 | A1 | | 8/1995 | |
| WO | 9521290 | A1 | | 8/1995 | |
| WO | 9533816 | A1 | | 12/1995 | |
| WO | 9610072 | A1 | | 4/1996 | |
| WO | 9614384 | A1 | | 5/1996 | |
| WO | 9616148 | A1 | | 5/1996 | |
| WO | 9633254 | A1 | | 10/1996 | |
| WO | 9700938 | A1 | | 1/1997 | |
| WO | 9742286 | A1 | | 11/1997 | |
| WO | 9743393 | A1 | | 11/1997 | |
| WO | 9800528 | A1 | | 1/1998 | |
| WO | 9803513 | A1 | | 1/1998 | |
| WO | 9804659 | A1 | | 2/1998 | |
| WO | 9805749 | A1 | | 2/1998 | |
| WO | 9811189 | A1 | | 3/1998 | |
| WO | 9818893 | A1 | | 5/1998 | |
| WO | WO-9906366 | A1 | * | 2/1999 | .......... C07C 407/00 |
| WO | 9919451 | A1 | | 4/1999 | |
| WO | 9931215 | A1 | | 6/1999 | |
| WO | 9932598 | A1 | | 7/1999 | |
| WO | 9964556 | A1 | | 12/1999 | |
| WO | 0042145 | A1 | | 7/2000 | |
| WO | 0042158 | A1 | | 7/2000 | |
| WO | 0078911 | A1 | | 12/2000 | |
| WO | 0144176 | A1 | | 6/2001 | |
| WO | 0187358 | A1 | | 11/2001 | |
| WO | 2005067741 | A1 | | 7/2005 | |
| WO | 2006016145 | A1 | | 2/2006 | |
| WO | 2006094232 | A1 | | 9/2006 | |
| WO | 2006131503 | A2 | | 12/2006 | |
| WO | 2007066302 | A2 | | 6/2007 | |
| WO | 2009071664 | A1 | | 6/2009 | |
| WO | 2009141548 | A2 | | 11/2009 | |
| WO | 2010050634 | A1 | | 5/2010 | |
| WO | 2011089313 | A2 | | 7/2011 | |
| WO | 2012080124 | A1 | | 6/2012 | |
| WO | WO-2014137605 | A1 | * | 9/2014 | ............ A01N 25/16 |

OTHER PUBLICATIONS

Mannan (Lees' Loss Prevention in the Process Industries, Fourth edition, Chapter 22—Storage, 2012) (Year: 2012).*

Wang et al. ("Thermal hazards of a green antimicrobial peracetic acid combining DSC calorimeter with thermal analysis equations," J Therm Anal Calorim, 2015, 119, pp. 2257-2267) (Year: 2015).*

Hub et al. ("Early on-line detection of exothermic reactions," Plant/Operations Progress, vol. 5, No. 5, 1986, 221-224) (Year: 1986).*

Spence et al. ("Reliable detection of runaway reaction precursors in liquid phase reactions," Plant/Operations Progress, vol. 7, No. 4, 1988, 231-235) (Year: 1988).*

English language machine translation of EP 626371 A (Year: 1994).*

2,6-Pyridinedicarboxylic acid SDS (Year: 2021).*

Baviera et al., "Report of the Scientific Committee of the Spanish Agency for Consumer Affairs, Food Safety and Nutrition (AECOSAN) in relation to the use of an antimicrobial aqueous solution containing hydrogen peroxide, acetic acid and peroxyacetic acid (23/17/15) as a processing aid on citrus fruits and tomatoes, and their wash water", Food Safety and Nutrition of the Scientic Committee on plenary session, 23 pages, May 18, 2016.

International Searching Authority, in connection with PCT/US2021/025030 filed Mar. 31, 2021, "The International Search Report and the Written Opinion of the International Searching Authority, or the Declaration", 11 pages, mailed Jul. 8, 2021.

Cefic, "Bulk Storage Guidelines," European Chemical Industry Council, Mar. 2012, Hydrogen Peroxide Subgroup, 50 pages.

Brooks et al., "Alkaline hydrogen peroxide bleaching of cellulose," Cellulose, Sep. 2000, vol. 7, No. 3, pp. 263-286.

Carboni-Oerlemans et al., "Hydrolase-catalysed synthesis of peroxycarboxylic acids: Biocatalytic promiscuity for practical applications," Journal of Biotechnology, Nov. 2006, vol. 126, pp. 140-151.

Chen, J., "Enhanced Alkaline Peroxide Bleaching of Softwood Kraft Pulps Using a New Activator," Journal of Pulp and Paper Science, Dec. 2001, vol. 27, No. 12, 4 pages.

Chung, L., "Coordinative Binding of Divalent Cations with Ligands Related to Bacterial Spores," Biophysical Journal, Jun. 1971, vol. 11, pp. 469-482.

Dannacher, JJ., "Catalytic bleach: Most valuable applications for smart oxidation chemistry," Journal of Molecular Catalysis A: Chemical, May 2006, vol. 251, pp. 159-176.

Database CAPLUS Chemical Abstracts Service, Accession No. 1960:97225, abstract of DE 1024514, "Oxidation of Organic Compounds with Hydrogen Peroxide in the Liquid Base," Feb. 1958, 6 pages.

Effkemann et al., "Peroxide analysis in laundry detergents using liquid chromatography," Analytica chimica acta, May 1998, vol. 363, pp. 97-103.

Helrich, Kenneth, "A.O.A.C. Use Dilution Methods," Official Methods of Analysis of the Association of Official Analytical Chemists, 15th Edition, 1990, pp. 135-136.

Helrich, Kenneth, "Agricultural Chemicals; Contaminants; Drugs," Official Methods of Analysis of the Association of Official Analytical Chemists, 15th Edition, 1990, 11 pages.

Helrich, Kenneth, "Germicidal and Detergent Sanitizing Action of Disinfectants," Official Methods of Analysis of the Association of Official Analytical Chemists, 15th Edition, 1990, pp. 138-140.

Katz, Jonathan, "Report: Fracking to Grow U.S. Frack Water-Treatment Market Nine-Fold by 2020," Industry Week, May 2012, 2 pages.

Klaas et al., "Biocatalytic peroxy acid formation for disinfection," Journal of Molecular Catalysis B: Enzymatic, Dec. 2002, vol. 19-20, pp. 499-505.

Klaas et al., "Lipase-catalyzed conversions of trimethylsilyl ethers: deprotection, acetylation, epoxidation and one-pot-multi-step reactions," Journal of Molecular Catalysis B: Enzymatic, Dec. 1999, vol. 7, No. 5-6, pp. 283-289.

Klaas et al., "Lipase-catalyzed preparation of peroxy acids and their use for epoxidation," Journal of molecular catalysis A: Chemical, Mar. 1997, vol. 117, No. 1-3, pp. 311-319.

Lee et al., "Hydrolytic stability of a series of lactam-based cationic bleach activators and their impact on cellulose peroxide bleaching," Cellulose, Jun. 2010, vol. 17, pp. 671-678.

Leistner, L., "Basic aspects of food preservation by hurdle technology," International Journal of Food Microbiology, Apr. 2000, vol. 55, pp. 181-186.

Leistner, L., "Principles and applications for hurdle technology," in: G.W. Gould, New Methods of Food Preservation, 1995, 23 pages.

(56) References Cited

OTHER PUBLICATIONS

Leveneur et al., "Synthesis of peroxypropionic acid from propionic acid and hydrogen peroxide over heterogeneous catalysts," Chemical Engineering Journal, Apr. 2009, vol. 147, pp. 323-329.
Maeda et al., "Assessment of Acyl Groups and Reaction Conditions in the Competition between Perhydrolysis and Hydrolysis of Acyl Resorufins for Developing an Indicator Reaction for Fluorometric Analysis of Hydrogen Peroxide," Chemical and Pharmaceutical Bulletin, Feb. 2002, vol. 50, pp. 169-174.
Malow et al., "Prediction of the self-accelerating decomposition temperature (SADT) for liquid organic peroxides from differential scanning calorimetry (DSC) measurements," Journal of Hazardous Materials, Apr. 2005, vol. A120, pp. 21-24.
Muurinen, Esa, "Organosolv Pulping," Dissertation presented to the faculty of technology, University of Oulu, Finland, Jun. 30, 2000, 25 pages.
Nowack, Bernd, "Environmental chemistry of phosphates," Water Research, Jun. 2003, vol. 37, No. 11, pp. 2533-2546.
Ogata et al., "Radical Scavenging Activities of Niacin-Related Compounds," Bioscience, biotechnology, and biochemistry, Jan. 2002, vol. 66, No. 3, pp. 641-645.
Ogata et al., "The Formation of Peracids by the Perhydrolysis with Alkaline Hydrogen Peroxide," Tetrahedron, Jan. 1967, vol. 23, No. 8, pp. 3327-3332.
Popov et al., "Critical Evaluation of Stability Constants of Phosphonic Acids," Pure and Applied Chemistry, Oct. 2001, vol. 73, No. 10, pp. 1641-1677.
Rizkalla et al., "Metal Chelates of Phosphonate-Containing Ligands," Talanta, Sep. 1980, vol. 27, No. 9, pp. 715-719.
Suchy et al., "Improving Alkaline Peroxide Delignification Using a Vanadium Activator," Pulping Conference, Oct. 25-29, 1998, Book 3, 15 pages.
Tsunokawa et al., "A Versatile Method for Preparation of O-Alkylperoxycarbonic Acids: Epoxidation with Alkyloxycarbonylimidazoles and Hydrogen Peroxide," Tetrahedron Letters, 1982, vol. 23, No. 20, pp. 2113-2116.
United Nations, "Recommendations on the Transport of Dangerous Goods, Manual of Tests and Criteria," vol. 1, 17th revised edition, 2011, 200 pages.
Yin et al., "Switching catalysis from hydrolysis to perhydrolysis in P. fluorescens esterase," Biochemistry, Mar. 2010, vol. 49, No. 9, pp. 1931-1942.
United Nations. "Recommendations on the Transport of Dangerous Goods." Model Regulations, vol. 1 & 2, 14th ed., United Nations, New York and Geneva, (2005): 1-937.

* cited by examiner

METHOD FOR QUENCHING PEROXYCARBOXYLIC ACID RUNAWAY REACTIONS

CROSS-REFERENCE TO RELATED APPLICATION

This application claims priority under 35 U.S.C. § 119 to Provisional Application U.S. Ser. No. 63/002,434, filed on Mar. 31, 2020, which is herein incorporated by reference in its entirety including without limitation, the specification, claims, and abstract, as well as any figures, tables, or examples thereof.

FIELD OF THE INVENTION

The invention relates to systems for quenching peroxycarboxylic acid and peroxide chemistry runaway reactions to provide safe and efficacious systems to prevent uncontrolled runaway reactions, such as decomposition reactions, of peroxycarboxylic acid and peroxide chemistry compositions. The systems provide prompt detection and dispensing of a stabilizer into a tank or other storage vessel containing a peroxide composition, peroxycarboxylic acid composition or a peroxycarboxylic acid-forming composition to stop a runaway reaction. Methods for quenching peroxide and peroxy carboxylic acid runaway reactions are also provided.

BACKGROUND OF THE INVENTION

Peroxy carboxylic acids have emerged as effective alternatives for cleaning, sanitizing, and disinfecting in various applications. In addition to performance benefits available from the peroxycarboxylic acids, a significant benefit is the safety of decomposition products being the corresponding carboxylic acid, hydrogen peroxide and water. Peroxycarboxylic acids can be provided in equilibrium or non-equilibrium compositions, prepared, and shipped ready for use, or generated onsite for applications of use. In applications where a peroxy carboxylic acid is formed, stored and/or transported there are safety precautions employed for the compositions. When peroxycarboxylic acids are stored in large quantities it is a particular challenge for the volume to shed decomposition heat in comparison to smaller quantities.

In some instances, contaminants, such as trace levels of materials such as alkalis, halides, organics, or transitional metals can cause decomposition reactions and result in an uncontrolled runaway reaction leading to a boil out of the contents. Most often iron or other metal contaminants are the cause. This can present a safety hazard as the reaction can produce large quantities of gas in a short time capable of boiling out the contents, with the potential to explode, releasing two phase gas and liquid flow of acidic, corrosive, and oxidizing materials from the storage vessel.

Due to the spontaneous decomposition tendency of peroxycarboxylic acids it is common to stabilize the composition by the addition of various chemicals, such as 1-Hydroxyethylidene-1,1-diphosphonic acid (HEDP) or Dipicolinic acid (DPA). However, only small quantities can be utilized in light of both practical and regulatory limits for these stabilizers, which are often included in the low range of about 10,000 ppm and 500 ppm, respectively. While these levels generally suffice for protection against nominal contamination levels, they are easily overwhelmed by contaminants that enter the formulae either via raw materials or poor plant/customer hygiene. They are also more easily overwhelmed in large volume containers such as 1000 L totes.

Various systems for the production and use of peroxycarboxylic acid solutions have utilized acids, such as sulfuric acid, acetic acid, citric acid, or nitric acid, to prevent peroxy carboxylic acid degradation within nonequilibrium composition to lower the pH and potentially quench a reaction. See US 2018/0042231. However, there are concerns with using many of these acids to slow the decomposition of a peracid as many of these are reactive with peracids and will produce exothermic decomposition.

These methods and systems can further include the use of stabilizers or chelating agents to bind contaminants or substances that otherwise would react with the peroxy carboxylic acid and/or hydrogen peroxide oxidizers. Stabilizers are most often used in equilibrium compositions to stabilize and prevent degradation of the peroxy carboxylic acid. See also US 2020/0323205. The use of stabilizers has also been recognized to provide value in complexing metal ion agents at temperatures in excess of 35° C.; however, WO 95/022816 teach it is preferred for aqueous bleaching composition comprising an organic peroxyacid to be produced at a temperature below 30° C. or in the alternative if reactions are above 35° C. they should be carried out in the absence of the metal ion complexing agents.

However, no sufficient solutions have been provided for runaway reactions by the prior art. Instead, there has been an emphasis on monitoring pressure and/or temperature of reactions to form peroxycarboxylic acids. For example, in US 2020/0323205, the use of pressure and/or temperature detects the potential for a runaway reaction. For example, the pressure monitoring could be accomplished by use of a differential pressure sensor within a feedback control loop, wherein a pressure reading exceeding a set point would cause a safety release valve and/or rupture disk to be employed or venting to occur. As a further example, it is disclosed that temperature can be monitored through use of temperature probes placed upstream and down-stream of the reaction, and if the downstream temperature is higher than the upstream temperature then this can trigger a safety shut off of the heater and pumps. Moreover, US 2020/0323205 utilizes heated reactions and cooling is taught as the method for quenching undesired reactions.

It is therefore an object of this disclosure to provide systems for quenching the earliest stages of an uncontrolled runaway decomposition reaction to interrupt and stop the reaction from taking place.

It is a further object of this disclosure to provide systems for quenching runaway decomposition reactions that are applicable for use in storage tanks and/or vessels and/or transport tanks and/or vessels.

It is a further object of the disclosure to provide systems for detecting the earliest stages of an uncontrolled runaway decomposition reaction.

It is another object of this disclosure to provide methods for quenching runaway decomposition reactions, including methods that allow continued use of the peroxycarboxylic acid composition.

Other objects, aspects and advantages of this invention will be apparent to one skilled in the art in view of the following disclosure, the drawings, and the appended claims.

SUMMARY OF THE INVENTION

In accordance with the background described herein, the described and other problems associated with the storage and production of peroxycarboxylic acid compositions are solved by a system and method for quenching peroxycarboxylic acid runaway reactions, in particular the quenching of industrial peroxycarboxylic acid auto catalyzed runaway reactions.

In embodiments, a system for quenching peroxide or peroxycarboxylic acid runaway reactions comprising: a first tank storing a peroxide composition, peroxy carboxylic acid composition or a peroxy carboxylic acid-forming composition: a second tank storing a stabilizer: at least one temperature probe housed in the first tank: a dispense module that dispenses the stabilizer from the first tank into the second tank; and a programmable controller for controlling the operation of the system to quench the runaway reactions in response to determining that the temperature measured by the temperature probe has reached (i) a first predetermined temperature, (ii) a predetermined increase in rate of temperature increase as a function of time, or (iii) a change in temperature of greater than about 25° F. (13.8° C.) over ambient temperature. Various embodiments of the system are disclosed herein.

In embodiments, methods of quenching a runaway reaction of a peroxide or peroxycarboxylic acid composition comprise: detecting (i) an increase in temperature or (ii) a predetermined increase in rate of temperature increase as a function of time, in a first tank, wherein the first tank contains a peroxide composition, a peroxy carboxylic acid composition or mixing a peroxy carboxylic acid-forming composition: dispensing a stabilizer into the first tank, wherein the stabilizer is housed in a second tank; and quenching the runaway reaction. Various embodiments of the methods are disclosed herein.

While multiple embodiments are disclosed, still other embodiments will become apparent to those skilled in the art from the following detailed description, which shows and describes illustrative embodiments. Accordingly, the drawings and detailed description are to be regarded as illustrative in nature and not restrictive.

Figure 1:
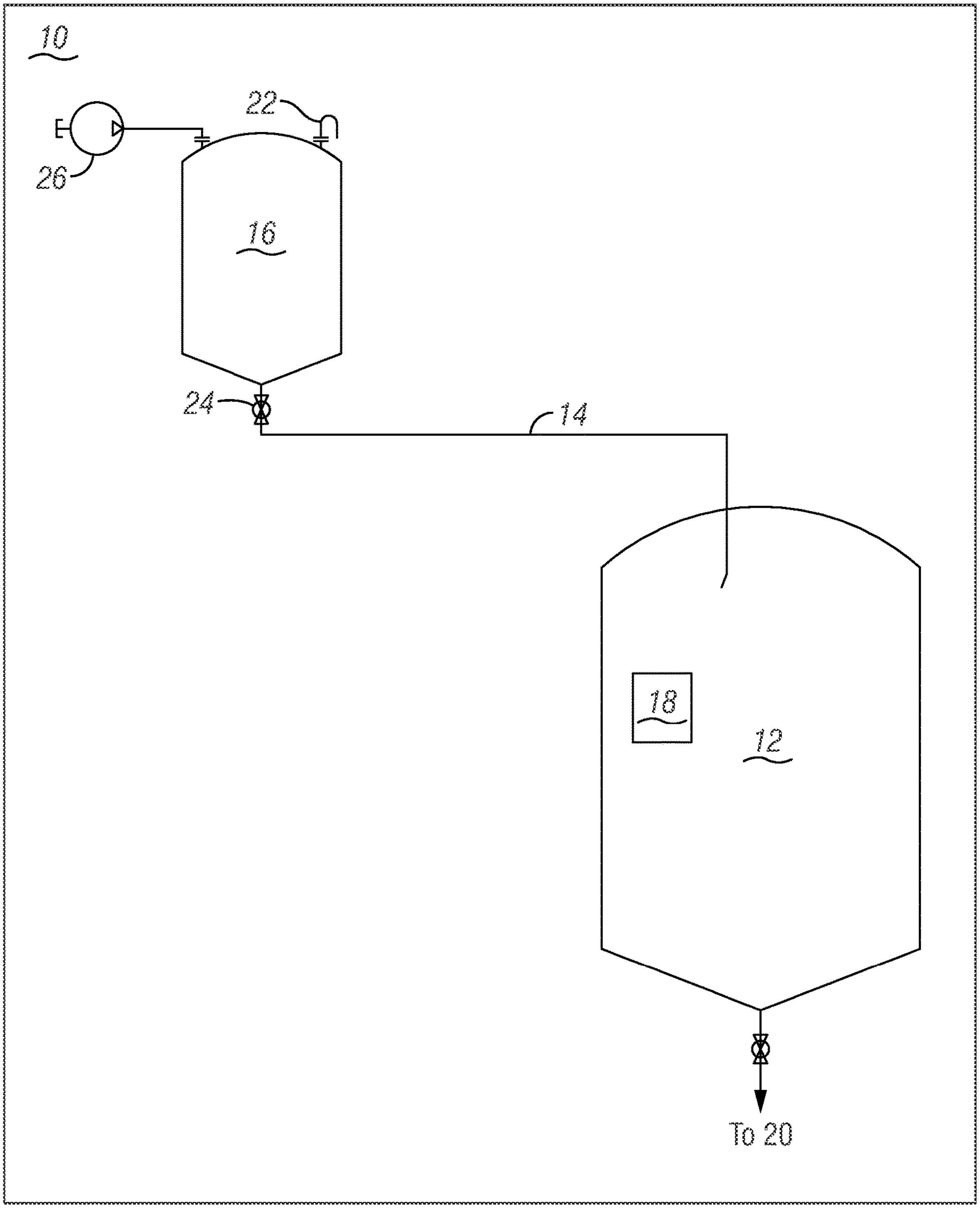
FIGS. 1-2 illustrate schematic views of systems for quenching runaway reactions, according to some aspects of the present disclosure.

Various embodiments of the present invention will be described in detail with reference to the drawings, wherein like reference numerals represent like parts throughout the several views. Reference to various embodiments does not limit the scope of the invention. Figures represented herein are not limitations to the various embodiments according to the invention and are presented for exemplary illustration of the invention.

DETAILED DESCRIPTION OF THE PREFERRED EMBODIMENTS

The embodiments are not limited to particular systems and methods for quenching runaway decomposition reactions, which can vary and are understood by skilled artisans. It has been surprisingly found that the systems and methods described herein for quenching runaway reactions are able to quench the reaction at the earliest stages and in some embodiments are able to use the peroxy carboxylic acid that was quenched with the stabilizer(s) providing a benefit of not having to discard the peroxycarboxylic acid composition.

It is further to be understood that all terminology used herein is for the purpose of describing particular embodiments only and is not intended to be limiting in any manner or scope. For example, as used in this specification and the appended claims, the singular forms "a," "an" and "the" can include plural referents unless the content clearly indicates otherwise. Further, all units, prefixes, and symbols may be denoted in its SI accepted form. Numeric ranges recited within the specification are inclusive of the numbers within the defined range. Throughout this disclosure, various aspects are presented in a range format. It should be understood that the description in range format is merely for convenience and brevity and should not be construed as an inflexible limitation on the scope of the invention. Accordingly, the description of a range should be considered to have specifically disclosed all the possible sub-ranges as well as individual numerical values within that range (e.g. 1 to 5 includes 1, 1.5, 2, 2.75, 3, 3.80, 4, and 5).

So that the present invention may be more readily understood, certain terms are first defined. Unless defined otherwise, all technical and scientific terms used herein have the same meaning as commonly understood by one of ordinary skill in the art to which embodiments of the invention pertain. Many methods and materials similar, modified, or equivalent to those described herein can be used in the practice of the embodiments without undue experimentation, but the preferred materials and methods are described herein. In describing and claiming the embodiments, the following terminology will be used in accordance with the definitions set out below.

The term "about," as used herein, refers to variation in the numerical quantity that can occur, for example, through typical measuring and liquid handling procedures used for making concentrates or use solutions in the real world; through inadvertent error in these procedures; through differences in the manufacture, source, or purity of the ingredients used to make the compositions or carry out the methods; and the like. The term "about" also encompasses amounts that differ due to different equilibrium conditions for a composition resulting from a particular initial mixture. Whether or not modified by the term "about", the claims include equivalents to the quantities.

The term "weight percent," "wt-%," "percent by weight," "% by weight," and variations thereof, as used herein, refer to the concentration of a substance as the weight of that substance divided by the total weight of the composition and multiplied by 100. It is understood that, as used here, "percent," "%," and the like are intended to be synonymous with "weight percent," "wt-%," etc.

The methods and systems may comprise, consist essentially of, or consist of the components and ingredients as well as other ingredients described herein. As used herein, "consisting essentially of" means that the methods and systems may include additional steps, components, or ingredients, but only if the additional steps, components, or ingredients do not materially alter the basic and novel characteristics of the claimed methods and compositions.

In communications and computing, a computer readable medium is a medium capable of storing data in a format readable by a mechanical device. The term "non-transitory" is used herein to refer to computer readable media ("CRM") that store data for short periods or in the presence of power such as a memory device.

One or more embodiments described herein can be implemented using programmatic modules, engines, or components. A programmatic module, engine, or component can include a program, a sub-routine, a portion of a program, or a software component or a hardware component capable of performing one or more stated tasks or functions. A module or component can exist on a hardware component independently of other modules or components. Alternatively, a module or component can be a shared element or process of other modules, programs, or machines.

Systems for Quenching Peroxycarboxylic Acid Runaway Reactions

Figure 2:
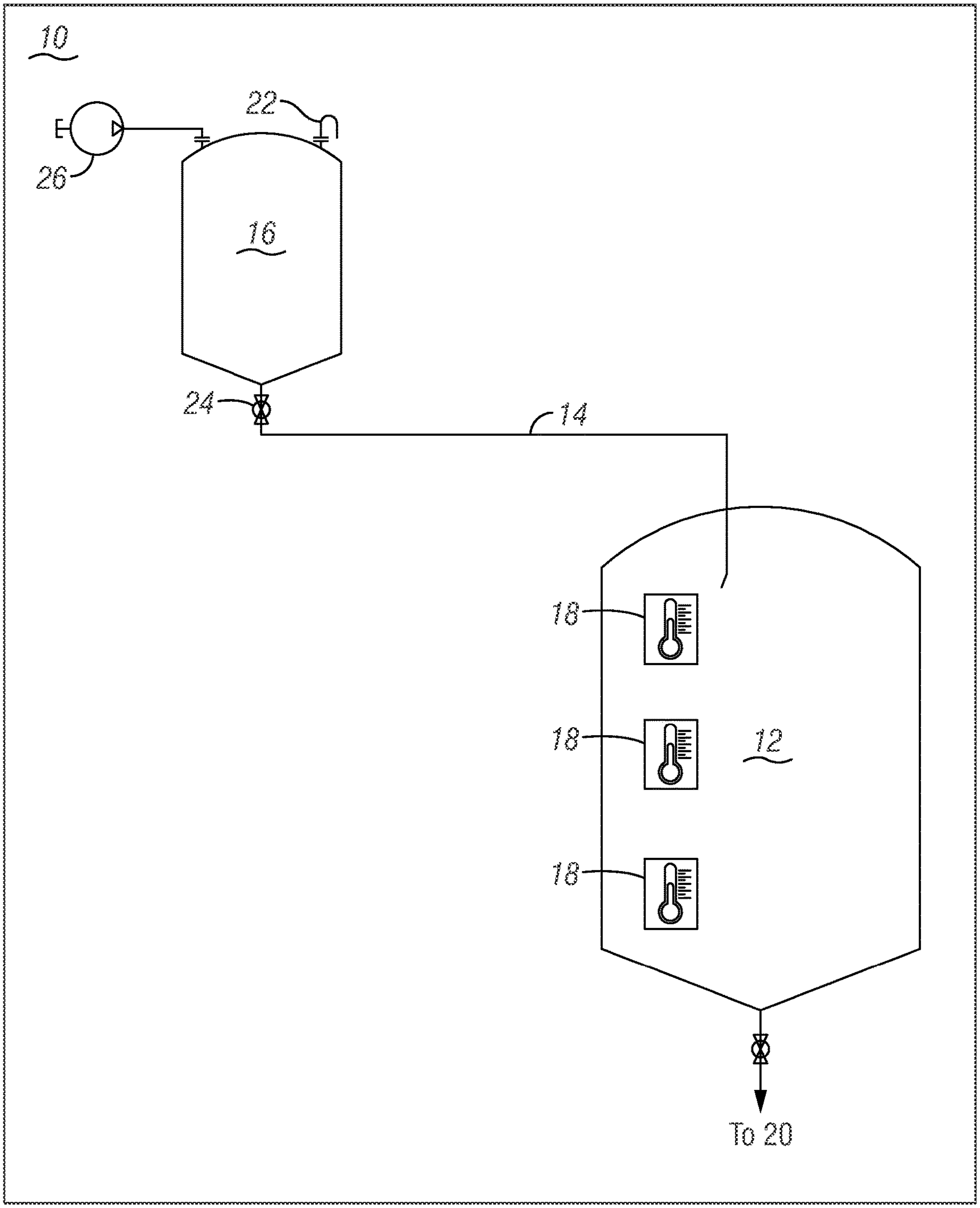
Figure 3:
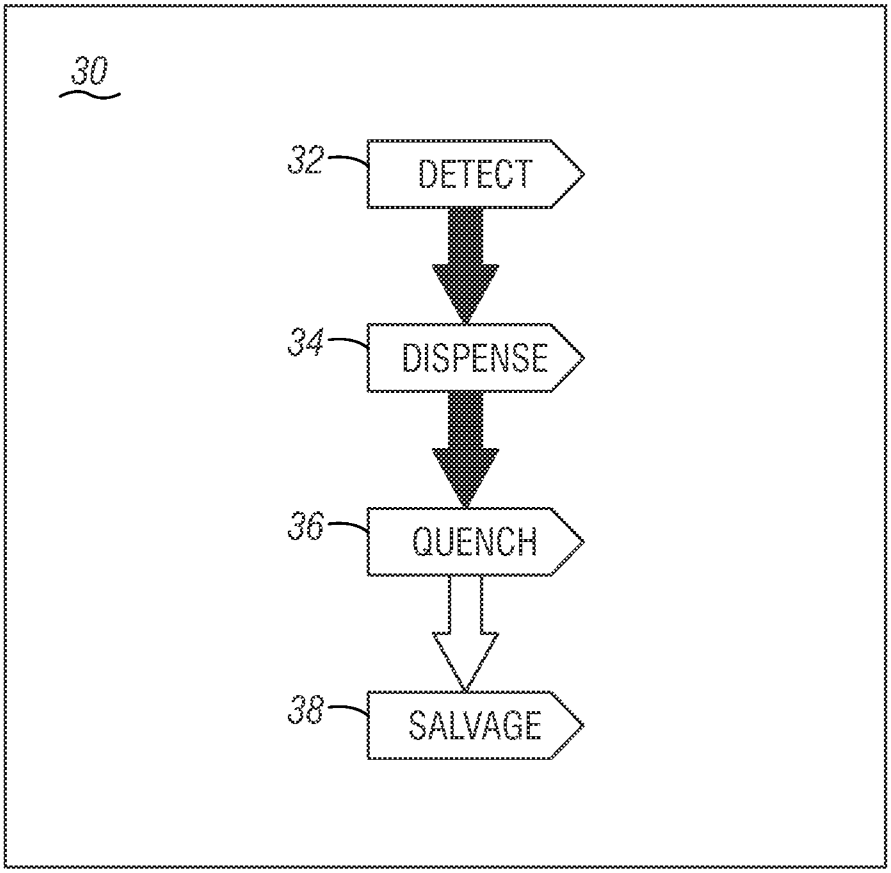
FIG. 3 depicts a flow chart of a method of controlling the system of FIGS. 1-2, said method to be carried out, at least in part, by a programmable controller.

Exemplary systems 10 for quenching peroxy carboxylic acid runaway reactions are shown in FIGS. 1-2 and include a first tank 12 storing a peroxide composition, peroxy carboxylic acid composition or a peroxy carboxylic acid-forming composition comprising a peroxide source, a carboxylic acid, and optionally catalysts and/or acidulants, a second tank 16 fluidly connected to, and in one embodiment positioned upstream from, the first tank 12 by way of a fluid connection 14, said second tank 16 storing a stabilizer, at least one temperature probe 18 housed in the first tank, a dispense module 24 that dispenses the stabilizer from the second tank into the first tank, a fluid collector, outlet, valve, fluid connection, or other suitable means 20 for outputting fluid from the first tank 12, and a programmable controller 30 (illustrated in FIG. 3) for controlling the operation of the system 10.

The first tank 12 for storing a peroxide composition, peroxy carboxylic acid composition or a peroxycarboxylic acid-forming composition is any type of tank, vessel, drum, cylinder, container, receptacle, bin, or the like. Storage tanks, and more particularly reservoirs, chambers, compartments, and/or cavities located therein, are commonly employed for holding volumes of peroxy carboxylic acid compositions for storage and/or shipment. Similarly, precursor chemicals and/or peroxy carboxylic acid-forming compositions can be held in separate reservoirs, chambers, compartments, and/or cavities of the same tank, or in more tanks, such as at a point of manufacturing and/or in situ generation of chemistry. The first tank 12 can be any shape, size, and material suitable for storing the peroxy carboxylic acid without introducing contaminants or substances known to react with the peroxycarboxylic acids. In some embodiments, the first tank 12 is a bulk storage tank, container, tote and/or drum. As referred to herein, bulk also includes intermediate sized bulk storage tanks, containers, totes and/or drums, such as sizes of at least about 250 gallons, 300 gallons, or larger.

The fluid connection 14 between the first tank 12 and the second tank 14 can be direct or indirect and can, by way of example, comprise a line, pipe, conduit, tube, port, opening, passage, and/or other suitable means of connection.

The second tank 16 for storing a stabilizer(s) for quenching the decomposition reactions is any type of tank, vessel, drum, cylinder, container, receptacle, bin, or the like. The second tank 16 can be any shape, size, and material suitable for storing the stabilizer(s) without introducing contaminants or substances known to react with peroxy carboxylic acids.

At least one temperature probe 18 is housed within the first tank 12 to monitor the temperature of the peroxide composition, peroxy carboxylic acid composition or peroxycarboxylic acid-forming composition stored in the first tank 12. In some embodiments, a plurality of temperature probes are located within the first tank (such as shown in FIG. 2 where more than one probe is depicted). In embodiments, at least two, three, four, five, six, or more temperature probes are located within the first tank 12. The number of temperature probes 18 will vary based upon the shape and size of the first tank 12. It is preferred to have a plurality of temperature probes 18 across all regions of the tank to measure for the earliest indications of changes in temperature of the peroxide composition, peroxy carboxylic acid composition or a peroxy carboxylic acid-forming composition.

Temperature probe(s) 18 can include any suitable type of thermal sensor/monitor for measuring temperature. For example, the thermal sensor/monitor can comprise transducer(s): thermistor(s): thermocouple(s): thermometer(s), such as infrared ("IR") guns; and/or the like. Temperature probes 18 can be coated with a compatible material that does not introduce contaminants into the system 10. Exemplary materials can include, for example, stainless steel (e.g. 316L stainless), alloys, such as nickel, molybdenum, chromium (e.g. Hasteloy C) and/or polymers such as fluoropolymers of tetrafluoroethylene (e.g. polytetrafluoroethylene (PTFE)), or the like.

Optionally, and by way of non-limiting examples, the means 20 for outputting fluid from the first tank 12 can be: (a) used to dose to an application of use, (b) put into a container for spraying, (c) for further processing, and/or the like: a vent 22, exhaust, opening, pressure release mechanism, or other suitable safety feature can be in the second tank 16, as shown in FIG. 1: the dispense module 24 can comprise or work in tandem with one or more of the following computer driven components: actuators, flow controls, flow meters, valves, and/or other suitable aspects of the system 10; and/or a pump 26 or series of pumps can be configured to pump the stabilizer into and/or from the second tank 26.

The programmable controller 30 can comprise a microprocessor, a microcontroller, an arithmetic logic unit ("ALU"), a central processing unit ("CPU"), and/or some other programmable computing device which serves as the electronic circuitry that carries out the instructions of computer programs. The programmable controller 30 performs the basic arithmetic, logic, controlling, and input/output ("I/O") operations specified by the instructions. The programmable controller 30 can be included in a tablet, telephone, handheld device, laptop, user display, display, and/or other suitable computing devices which allow for input and output of electronic functions.

In other words, the controller 30 is configured, via logic circuits, memory, operating systems, compilers, and/or other electrical arrangements or programmatic modules, to control the system 10. For example, and with reference to FIG. 3, the controller 30 continuously monitors for and thus is able to detect (illustrated in FIG. 3 as detect step 32) when the temperature probe(s) 18 reaches (i) a first predetermined temperature, (ii) a predetermined increase in rate of temperature increase as a function of time, or (iii) a change in temperature of greater than about at least 25° F. (13.8° C.) above ambient temperature. If such a scenario exists, the controller 30 can then instruct the dispense module 24 to dispense (illustrated in FIG. 3 as dispense step 34) the stabilizer from the second tank 16 into the first tank 12 and thereby quench, interrupt, or stop (illustrated in FIG. 2 as quench step 34) runaway reactions from taking place and/or progressing.

By way of example only, the controller 30 can control the operation of the system for quenching the runaway reactions by sensing and recording of data, opening/closing of valves in the system, activating pumps and/or other actuators within the system 10, and timing of the operations, together with providing associated warnings, safety checks and historical data.

It should be appreciated that the controller may be any type or make of controller 30 known to those skilled in the art. Beneficially, the controller 30 is programable such that it is programmed according to a user's location, preferred end use application, and/or environment where the peroxide or peroxycarboxylic acid compositions are stored and/or where a peroxycarboxylic acid-forming composition is generated and/or stored prior to use. In some embodiments, the user's location can be determined through geotagging, or automatically determining location through the use of a global positioning system ("GPS") receiver. In such embodiments, it is recognized that a programmable controller 30 is in communication, potentially wired, wireless, or a combination thereof, with the temperature probes 18 in the first tank 12 to detect either an increase in temperature within the first tank 12 and/or the reaching of a first (and/or second or more) predetermined temperature or detecting a predetermined increase in rate of temperature increase as a function of time. It is also to be appreciated that the controller 30 is in communication, potentially wired, wireless, or a combination thereof, with the dispense module 24, actuators, flow controls, flow meters, valves, and/or other aspects of the system 10 to control the operation of the system 10 and to quench the runaway reactions which are detected according to the changes in temperature measured by the temperature probes.

The controller 30 can be communicatively connected to one or more display devices or modules with various status indicators, such as light emitting diodes ("LEDs"). To interface with the user, the one or more display devices, modules, or even the controller 30 itself will preferably include a graphical user interface ("GUI"). However, it is also to be appreciated other various user interfaces ("UI") can be used, such as those with audio communications means (e.g. speakers, microphones, headphones, etc.), typical computer input/output means (e.g. computer mice, keyboards, touchscreens, etc.), and/or mechanical input/output means (e.g. knobs, dials, switches, buttons, etc.). For example, status indicators can indicate the current operation of a peroxycarboxylic acid reaction to generate a peroxy carboxylic acid composition. As a further example, the status indicators can indicate a current temperature (or average temperature of the zones) of the first tank, or other status of the system (e.g. status of the quenching reaction itself). It should be appreciated that the status indicators may be used for any other purpose related to operating characteristics of the system.

In some embodiments the GUI is used to input commands into the controller 30 and to provide a computer-assisted means through which operators can set up and deploy the quenching system into operation in an intended environment. In some embodiments, the GUI and the status indicators provide operators with functionality to monitor operation of the tanks for storage and/or generation of the peroxide or peroxy carboxylic acid compositions by displaying information relating to the temperature (or other measurements, e.g. pressure) that are monitored by the controller. In still other embodiments, the GUI is used only to alert an operator of the temperature (or other measurements, e.g. pressure) that are monitored by the controller, and the subsequent steps for quenching of the runaway reaction are fully automated and do not require further operator authorization to ensure the reaction is timely quenched.

Figure 5:
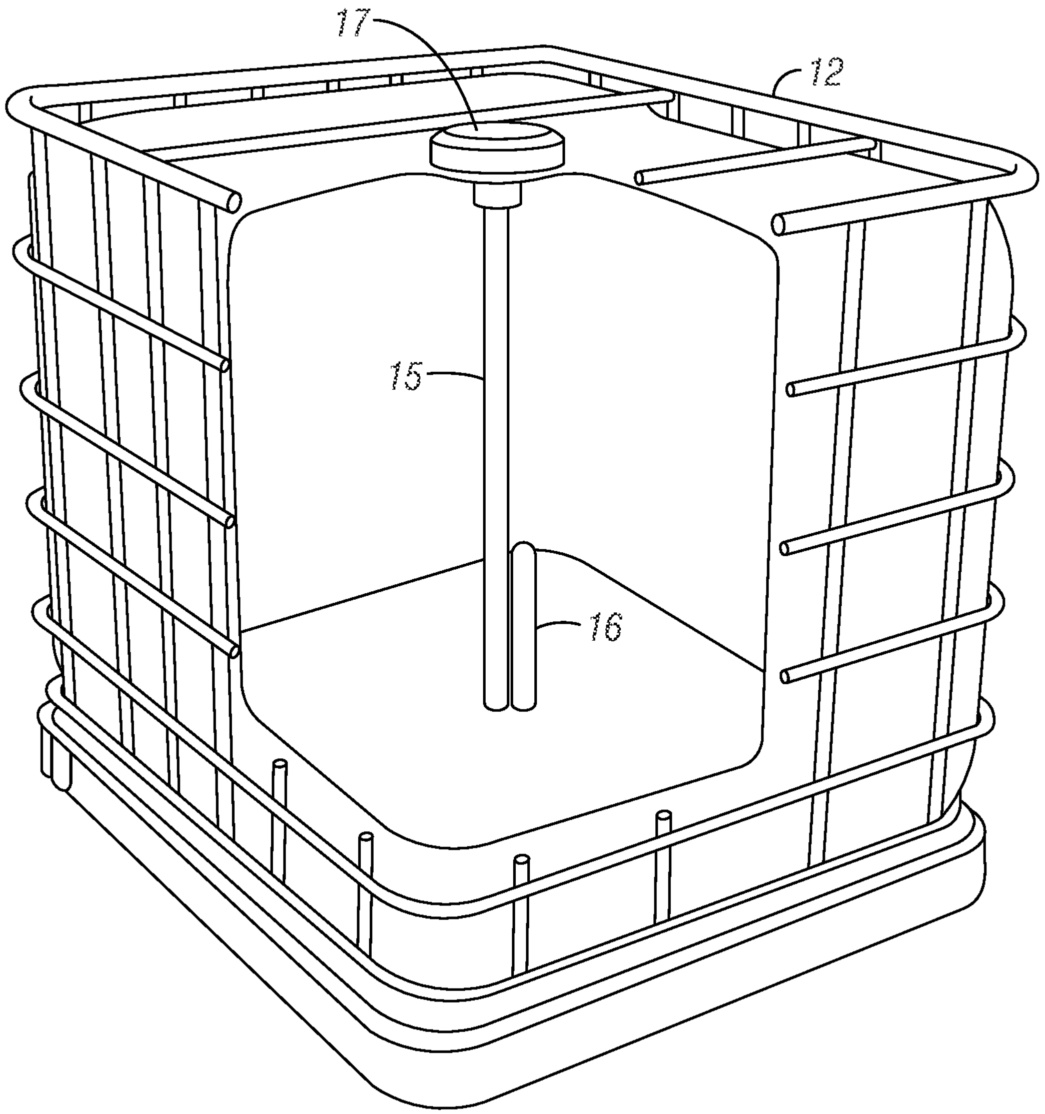
FIGS. 5-6 illustrate schematic views of systems for quenching runaway reactions in additional types of storage and/or transport vessels, according to some aspects of the present disclosure.
Figure 6:
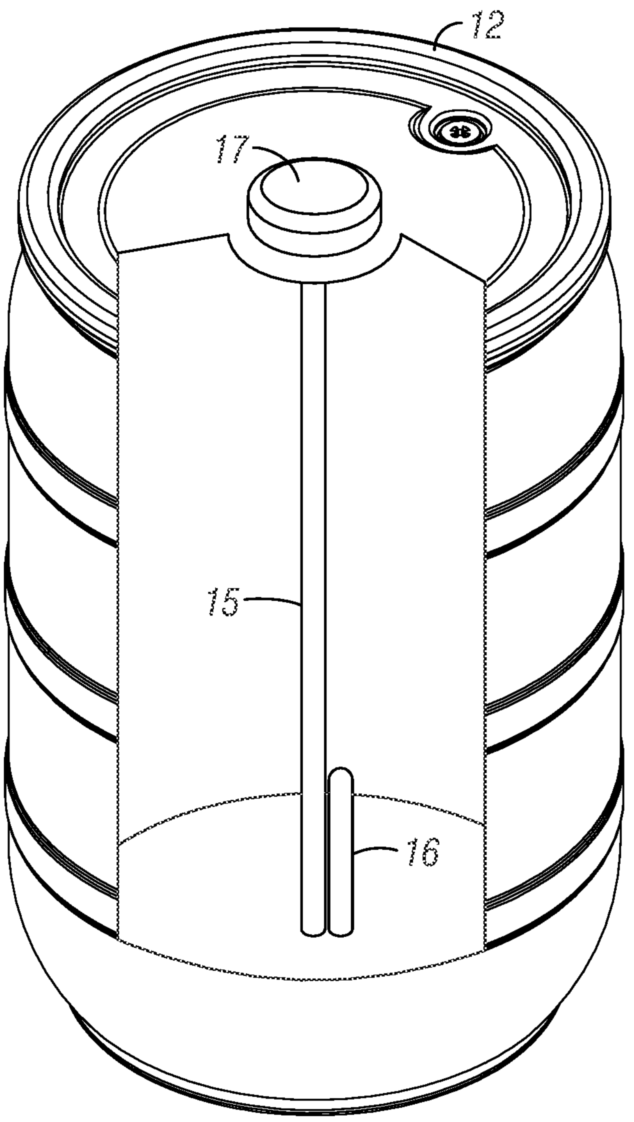

In further embodiments, systems 10 for quenching peroxycarboxylic acid runaway reactions (e.g. FIGS. 5-6) can be provided in a manner that does not include the temperature probes 18 and/or programmable controller 30. In such embodiments, there can be a tank 12 storing a peroxide composition, peroxycarboxylic acid composition or a peroxy carboxylic acid-forming composition comprising a peroxide source, a carboxylic acid, and optionally catalysts and/or acidulants, and a vessel 16 fluidly connected to or disposed or housed within the tank 12. In an embodiment the fluid connection can be a vessel disposed within or adjacent to the tank 12, such that the vessel 16 storing the stabilizer, could for example be coated in a substance (e.g. wax or wax-like substance) that melts and/or disintegrates to dose the stabilizer into the tank 12 upon a sufficient elevation of temperature within the tank 12.

Such an embodiment, without the temperature probe(s) and/or any automated dispense module allows for the dosing of the stabilizer from the second tank into the first tank. In the FIGS. 5-6, the tank 12 is a storage and/or transport container, e.g. tote (FIG. 5), drum (FIG. 6), or the like, and the vessel 16 containing the stabilizer is connected to a tube or probe 15 that is in contact with the peroxide composition, peroxycarboxylic acid composition or peroxy carboxylic acid-forming composition. The probe 15 and the vessel 16 storing the stabilizer may be affixed to a lid or other opening 17 for the tank 12. Such embodiments depicted in FIGS. 5-6 ensure that when the tank 12 is closed and there is the potential for a runaway reaction that would cause an increase in temperature in the tank 12, the vessel 16 storing the stabilizer will melts and/or disintegrates and thereby dose the stabilizer into the tank 12. As one skilled in the art will appreciate, the particular material that makes up the vessel 16 storing the stabilizer is design to melt and/or disintegrate upon a sufficient elevation of temperature within the tank to indicate the initiation of a potential runaway reaction, namely a temperature of 45° C., 50° C., 55° C., or 50°-55° C.

The material is inert and compatible with the peroxide composition, peroxy carboxylic acid composition or peroxy carboxylic acid-forming composition. This temperature would melt the inert material that makes up at least a portion of the vessel 16. As one can envision from the description herein, either the entirety of the vessel 16 or a portion of the vessel is made of the material that will melt or disintegrate upon the elevated temperature within the tank 12. In some embodiments the vessel 16 could be made of plastic tubing that is compatible with the peroxide composition, peroxycarboxylic acid composition or peroxycarboxylic acid-forming composition (e.g. PVC), and the plastic tubing is capped inside one or both ends (i.e. a plug) with a wax or peroxy species compatible plastic. The size of the vessel 16 will depend on the size of the tank 12 as it is sized to hold sufficient stabilizer to quench a reaction in the particular tank 12 (i.e. tote or drum). In an exemplary, non-limiting embodiment a vessel large enough to contain approximately 2 kg of the stabilizer DPA could be housed within a 1000 kg tote (the tank 12).

Additional embodiments (not depicted) without the temperature probe(s) and/or any automated dispense module can include encapsulated stabilizer in fluid connection (e.g. contained within the tank 12) with the peroxide composition, peroxy carboxylic acid composition or peroxycarboxylic acid-forming composition housed within the tank 12. The encapsulating material that prevents contact of the stabilizer with the peroxy species maintains the separation until an increase in temperature, namely a temperature reaching 45° C. 50° C., 55° C., or 50°-55° C. The encapsulating material is also compatible with the peroxide composition, peroxy carboxylic acid composition or peroxy carboxylic acid-forming composition. This temperature would melt the material that encapsulates the stabilizer.

Stabilizers

The system and methods described provide a stabilizer to the peroxide composition, peroxycarboxylic acid composition, or peroxycarboxylic acid-forming composition to quench (i.e. stop) a runaway decomposition reaction. Beneficially, the stabilizer(s) can be added by the system and methods during the early stages of an uncontrolled runaway decomposition reaction in order to quench or interrupt and stop the reaction from taking place. In some embodiments more than one stabilizer can be added by the system.

In an embodiment, the stabilizer is a phosphoric acid ($H_3PO_4$) or salt thereof, pyrophosphoric acid or salt thereof, phosphonic acid or salt thereof, or a pyridine carboxylic acid, a salt thereof or derivative thereof. An exemplary stabilizer is 1-hydroxyethylidene-1,1-diphosphonic acid (HEDP) or a salt thereof. Further exemplary stabilizers include aminotrimethylene phosphonic acid, ethylene diamine tetramethylene phosphonic acid, hexamethylene diamine tetramethylene phosphonic acid, diethylene triamine tetramethylene phosphonic acid.

In an embodiment, the stabilizer is a pyridine carboxylic acid, a salt thereof or derivative thereof. Exemplary stabilizers include 2,6-pyridine (mono or di) carboxylic acids, including 2,6-pyridinedicarboxylic acid (DPA). The 2,6-pyridinedicarboxylic acid has the following structure:

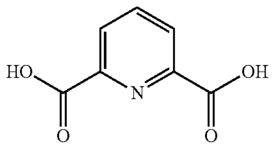 [SMILES: O=C(O)c1cccc(C(=O)O)n1]

In a further aspect, the 2,6-pyridine (mono or di) carboxylic acids can include 2,6-pyridine (mono or di) carboxylic acid oxides, shown below as the 2,6-pyridinedicarboxylic acid oxide having the following structure:

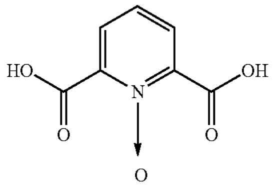 [SMILES: O=C(O)c1cccc(C(=O)O)n1 ; O]

Additional pyridine carboxylic acid derivatives include 3-pyridinecarboxylic acid (niacin, nicotinic acid, Vitamin B3), 4-pyridinecarboxylic acid (isonicotinic acid), 5-pyridinecarboxylic acid, 3,4-pyridinedicarboxylic acid, 3,5-pyridinedicarboxylic acid (dinicotinic acid), 4,5-pyridinedicarboxylic acid, 3,4,5-pyridinetricarboxylic acid, oxides thereof, and/or salts. The pyridine carboxylic acids, salts thereof, or derivatives thereof can have the following structure:

(I)

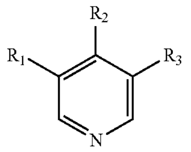

wherein $R_1$, $R_2$ and $R_3$ are independently COOH or H, or a salt thereof. Exemplary structures include the following:

(Ia)

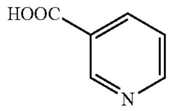

(Ib)

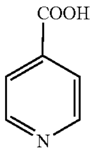

(Ic)

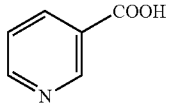

(Id)

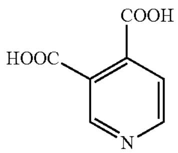

(Ie)

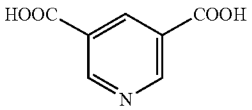

(If)

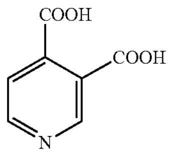

-continued (Ig)

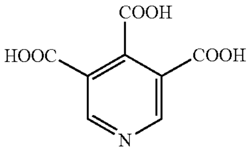

In a further aspect, the pyridine carboxylic acids can include pyridine carboxylic acid oxides having the following structure:

(II)

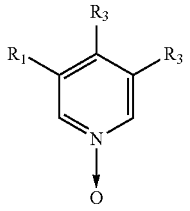

wherein $R_1$, $R_2$ and $R_3$ are independently COOH or H, or a salt thereof. Exemplary structures include the following:

(IIa)

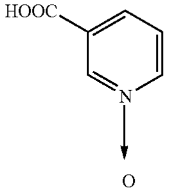

(IIb)

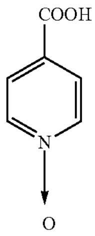

(IIc)

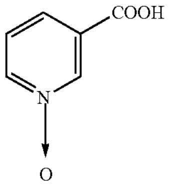

(IId)

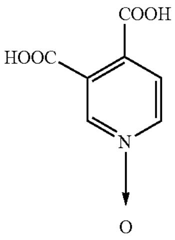

-continued (IIe)

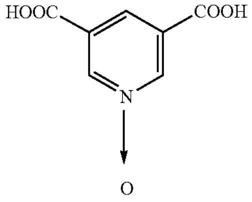

(IIf)

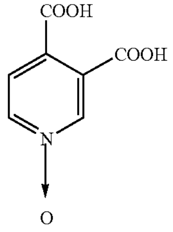

(IIg)

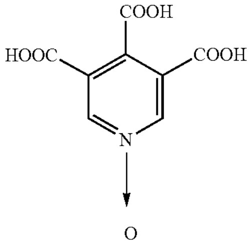

In an embodiment, a combination of stabilizers is employed. In an exemplary embodiment, a combination of 1-hydroxyethylidene-1,1-diphosphonic acid or a salt thereof and 2,6-pyridinedicarboxylic acid is employed as the stabilizers.

In an embodiment, the stabilizer(s) can be provided as a liquid or a free-flowing solid. In an embodiment, the stabilizer(s) can be provided as a solid, such as a solid block, that would first require dissolution before being dispensed into the first tank housing the peroxide composition, peroxycarboxylic acid composition, or peroxycarboxylic acid-forming composition to quench a runaway decomposition reaction.

Without being limited to a particular mechanism of action the use of the stabilizers to quench a decomposition reaction, such as that caused by iron or other contaminants, overcomes the kinetics of the reaction. One skilled in the art would expect for a stabilizer, such as a phosphoric acid or salt thereof, to bind to the contaminant (e.g. iron) in a stoichiometric manner and not exponential in its ability to quench the decomposition reactions as the stabilizer should bind catalytically and quench the decomposition reaction. However, the stabilizers are shown to be able to quench (i.e. stop) the reaction and therefore provide more than preventative action. Instead the stabilizers provide kinetically exponential effects in stopping the runaway decomposition reactions.

As a further benefit, the stabilizer can remain in the peroxy species containing composition (e.g. peroxycarboxylic acid composition) after the quenching reaction as they are compatible with the compositions. This is a further benefit to being able to salvage and use the compositions following the methods of quenching a runaway reaction, as suggested by the optional (hollow arrow) salvage step 38 in FIG. 2.

Peroxy Species

The system and methods described provide the stabilizer into a peroxy species, which can include a peroxide composition, a peroxy carboxylic acid composition or peroxycarboxylic acid-forming composition to quench a runaway decomposition reaction.

In embodiments, a single peroxy species is employed, as such reaction is likely to occur in a storage tank or vessel containing the peroxy species. However, in some embodiments more than one peroxy species can be employed, such as a mixed peroxy carboxylic acid composition. As used herein, the terms "mixed" or "mixture" when used relating to the peroxy species can include any combination thereof. However, in certain embodiments a mixed peroxy carboxylic acid composition is employed and includes more than one peroxy carboxylic acid.

According to the invention, a peroxy carboxylic acid (i.e. peracid) is included. As used herein, the term "peracid" may also be referred to as a "percarboxylic acid," "peroxy carboxylic acid" or "peroxyacid." Sulfoperoxycarboxylic acids, sulfonated peracids and sulfonated peroxy carboxylic acids are also included within the terms "peroxy carboxylic acid" and "peracid" as used herein. The terms "sulfoperoxycarboxylic acid," "sulfonated peracid," or "sulfonated peroxy carboxylic acid" refers to the peroxy carboxylic acid form of a sulfonated carboxylic acid, such as those disclosed in U.S. Pat. Nos. 8,344,026, 8,809,392 and 9,359,295, each of which are incorporated herein by reference in their entirety. As one of skilled in the art appreciates, a peracid refers to an acid having the hydrogen of the hydroxyl group in carboxylic acid replaced by a hydroxy group. A peroxy carboxylic acid includes any compound of the formula R—(COOOH) n in which R can be hydrogen, alkyl, alkenyl, alkyne, acrylic, alicyclic group, aryl, heteroaryl, or heterocyclic group, and n is 1, 2, or 3, and named by prefixing the parent acid with peroxy. Preferably R includes hydrogen, alkyl, or alkenyl.

Exemplary peroxy carboxylic acids include varying lengths of peroxy carboxylic acids (e.g. C1-22) and they can be prepared from any known method of reaction, whether producing equilibrium or non-equilibrium peroxy carboxylic acid compositions. As an example, an acid-catalyzed equilibrium reaction between a carboxylic acid and hydrogen peroxide can provide a peroxycarboxylic acid composition. Alternatively, an auto-oxidation of aldehydes or reaction of hydrogen peroxide with an acid chloride, acid anhydride, carboxylic acid anhydride, sodium alcoholate or alkyl and aryl esters can provide a peroxy carboxylic acid composition. Still further, non-equilibrium reactions can be used such as those disclosed in U.S. Pat. Nos. 8,846,107 and 8,877,254, which are incorporated herein by reference in their entirety.

In some embodiments, a peroxycarboxylic acid includes at least one water-soluble peroxy carboxylic acid in which R includes alkyl of 1-22 carbon atoms. For example, in one embodiment, a peroxycarboxylic acid includes peroxyacetic acid. In another embodiment, a peroxycarboxylic acid has R that is an alkyl of 1-22 carbon atoms substituted with a hydroxyl group or other polar substituent such that the substituent improves the water solubility. Methods of preparing peroxyacetic acid are known to those of skill in the art including those disclosed in U.S. Pat. No. 2,833,813, which is herein incorporated herein by reference in its entirety.

As referred to herein a peroxycarboxylic acid-forming composition can include a peroxy carboxylic acid composition that includes a peroxide source and a carboxylic acid (or a precursor). Optionally, the peroxy carboxylic acid composition could include stabilizers, acid catalysts, acidulants, surfactants, hydrotropes, solvents, defoaming agents as well as tracing compounds for analytical monitoring.

Various commercial formulations of peroxycarboxylic acids are available, including for example peroxyacetic acid (approximately 15%) available as EnviroSan (Ecolab, Inc., St. Paul MN). Most commercial peroxy carboxylic acids solutions state a specific peroxy carboxylic acid concentration without reference to the other chemical components in a use solution. However, it should be understood that commercial products, such as peroxyacetic acid, will also contain the corresponding carboxylic acid (e.g. acetic acid), hydrogen peroxide and water.

In an embodiment, any suitable C1-C22 peroxycarboxylic acid can be used. In some embodiments, the C1-C22 peroxycarboxylic acid is a C2-C20 peroxy carboxylic acid. In other embodiments, the C1-C22 peroxycarboxylic is a C1, C2, C3, C4, C5, C6, C7, C8, C9, C10, C11, C12, C13, C14, C15, C16, C17, C18, C19, C20, C21, or C22 carboxylic acid. In an embodiment employing a peroxycarboxylic acid the composition can have any ratio of hydrogen peroxide to peroxycarboxylic acid. In some embodiments, the ratio of hydrogen peroxide to peroxycarboxylic acid is from about 0:10 to about 10:0, or from about 0.5:10 to about 10:0.5.

Indicators for Delivery of Stabilizer

In some embodiments, the stabilizer can be combined with a dye. Preferred dyes include inert dyes to provide a visual indicator of the activation of the stabilizer and the methods described herein. This would beneficially provide a visual indicator of the dosing or release of the stabilizer into a vessel containing the peroxide composition, peroxy carboxylic acid composition or peroxy carboxylic acid-forming composition. This embodiment is particularly beneficial in tanks (e.g. storage and/or transport vessels) that may not have the temperature probes to detect a runaway reaction. This embodiment is further beneficial in tanks that are made of materials (e.g. natural HDPE or other material) that you can see into the tank as opposed to a dark colored tank.

Methods

Methods for quenching an uncontrolled runaway decomposition reaction to interrupt and stop the reaction from taking place are provided. The methods employing the systems beneficially stop the reaction at very early stages to minimize any danger to the system and/or users, such as those handling storage tanks and/or vessels and/or transport tanks and/or vessels containing the peroxide composition, a peroxy carboxylic acid composition or peroxycarboxylic acid-forming composition. The methods also beneficially allow continued use of the peroxide composition, a peroxycarboxylic acid composition or peroxy carboxylic acid-forming composition.

The methods of quenching a runaway reaction of a peroxide composition or a peroxy carboxylic acid composition include a first step of detecting an increase in temperature or an increase in the rate of increase in temperature. In an embodiment, there is detected in the first tank an increase in temperature of at least 25° F. (13.8° C.) above ambient temperature or a first predetermined temperature by a temperature probe housed in a first tank, wherein the first tank contains a peroxide composition, a peroxy carboxylic acid composition or a peroxy carboxylic acid-forming composition. In an embodiment, there is detected in the first tank a predetermined increase in rate of temperature increase as a function of time, wherein the first tank contains a peroxide composition, a peroxy carboxylic acid composition or a peroxy carboxylic acid-forming composition. The increase in rate of temperature increase is a positive change in the rate of temperature increase as a function of time (also understood as a positive second derivative or temperature per unit time). One skilled in the art will ascertain that an increase in the magnitude of the change in temperature as a function of time is an approach that protects the system from false positives in the detection step. For example, if the probe(s) in the first tank have a warm raw material transferred into it, a simple threshold criteria for a first predetermined temperature could trigger a quench that is not required as there is no runaway reaction. Instead, the dTemp/dTime values should be getting smaller and only an actual runaway reaction can cause increases in the dTemp/dTime values and therefore trigger the quenching as described herein.

The measurement of changes in temperature of the tank housing the peroxy species described herein is achieved by the temperature probe(s) housed within the tanks. The measurements of changes in temperature can be a single measurement of any one temperature probe or an average of a plurality of temperature probes, based on the programmable controller for the system.

In some embodiments, a change in temperature of at least 25° F. (13.8° C.) above ambient temperature is a measurement according to the system of the initiation of a runaway reaction. In some embodiments, a first predetermined temperature of 104° F. (40° C.), 45° C., 50° C. or 55° C. is a measurement according to the system of the initiation of a runaway reaction. As one skilled in the art will ascertain from the disclosure herein, the programmable controller can also allow a user to program at number of additional predetermined temperatures to measure according to the system to initiate the methods of quenching a runaway reaction. In an embodiment, the temperature measurements by the temperature probes indicate the temperature of the peroxy species housed in the first tank is approaching or has exceeded the self-accelerating decomposition temperature (SADT) value or is approaching an increase in temperature that would exceed the SADT.

Upon the measurement of the change in temperature of at least 25° F. (13.8° C.) above ambient temperature or the measurement of the first (or any additional) predetermined temperatures, the system dispenses the stabilizer into the first tank wherein the temperature probes indicated a runaway reaction has begun. The stabilizer is housed in a second tank and is dispense into the first tank to quench the runaway reaction. Beneficially, these measurements of change in temperature and/or predetermined temperatures initiate the dispensing of the stabilizer to the first tank at the very early stages of an uncontrolled runaway decomposition reaction in order to quench and stop the dangerous reaction from taking place. As the rate of temperature change in a runaway reaction will increase over time (i.e. accelerates), the early or initial detection of the increase in temperature beneficially allows the early detection of the runaway reaction.

In embodiments, the stabilizer is added to a first tank by any dosing, such as pumping the stabilizer from a second tank or otherwise adding a source of the stabilizer to the first tank. In an embodiment, the stabilizer could be loaded into a tube or other means that can be dosed, injected, or otherwise added to the first tank. For example, a loaded tube containing the stabilizer could be injected after fitting the tube into an opening (e.g. fitted on a thread opening). Any suitable way of adding the stabilizer into the first tank is embodied by the described systems and methods.

In alternative embodiments, the dosing of the stabilizer is not measured by a change in temperature. Instead, the increase in temperature within a tank or vessel will cause the dispensing of the stabilizer through the melting or disintegrating of a vessel housing the stabilizer (and optionally a dye). Upon reaching a predetermined temperature (e.g. 40° C., 50° C., or 55° C.) that causes at least a portion of the vessel housing the stabilizer to melt and/or disintegrate, the stabilizer is in contact with the peroxy species to quench the reaction. In this embodiment the dosing of the stabilizer is quick as the vessel housing the stabilizer is already submerged in the tank housing the chemistry undoing the exothermic reaction.

In embodiments, the stabilizer is added to the first tank within about 5 seconds, 10 seconds, or about 15 seconds (or any predetermined amount of time by the programmable controller) of the detected temperature changes or predetermined temperature(s) by the system.

In embodiments, the stabilizer is a phosphoric acid or salt thereof, pyrophosphoric acid or salt thereof, phosphonic acid or salt thereof, or a pyridine carboxylic acid, a salt thereof or derivative thereof. In some embodiments, the stabilizer comprises 1-hydroxyethylidene-1,1-diphosphonic acid (HEDP) or a salt thereof and/or 2,6-pyridinedicarboxylic acid. In embodiments, the stabilizer is a liquid, solid, or a powder. In embodiments, the stabilizer is dosed at a rate of at least about 2 wt-% based on the weight of the composition in the first tank, namely the peroxide composition, peroxy carboxylic acid composition or peroxycarboxylic acid-forming composition. In other embodiments, the stabilizer is dosed at any suitable concentration. In some embodiments, the stabilizer is dosed at a rate of at least about 2 wt-%, about 2 wt-% to about 10 wt-%, about 2.5 wt-% to about 10 wt-%, or about 2.5 wt-% to about 5 wt-%, based on the weight of the composition in the first tank.

In some embodiments, a dye or visual indicated is also included with the stabilizer to provide a visual indicator of the activation of the stabilizer and the methods described herein. This beneficially provides a visual indicator of the dosing or release of the stabilizer into a vessel containing the peroxide composition, peroxycarboxylic acid composition or peroxycarboxylic acid-forming composition.

In embodiments, the quenching of the peroxide composition, a peroxy carboxylic acid composition or peroxycarboxylic acid-forming composition beneficially do not consume the peroxy species. Unlike a decomposition reaction where the peroxy species is consumed, the quenching stops this process and the peroxy species remain intact in the compositions. This allows for the salvaging or continued used of the compositions and/or safe disposal of the compositions as opposed to conventional need to discard a consumed chemistry following a runaway decomposition reaction. In an embodiment, from about 80% to about 95% of the peroxy species in the treated peroxide composition, peroxy carboxylic acid composition and/or peroxycarboxylic acid-forming composition are retained and able to be used in the desired application of use. In an embodiment, at least about 80%, 85%, 90% %, 95%, or greater of the peroxy species in the treated peroxide composition, peroxycarboxylic acid composition and/or peroxycarboxylic acid-forming composition are retained and able to be used in the desired application of use.

EXAMPLES

Embodiments of the present invention are further defined in the following non-limiting Examples. It should be understood that these Examples, while indicating certain embodiments of the invention, are given by way of illustration only. From the above discussion and these Examples, one skilled in the art can ascertain the essential characteristics of this invention, and without departing from the spirit and scope thereof, can make various changes and modifications of the embodiments of the invention to adapt it to various usages and conditions. Thus, various modifications of the embodiments of the invention, in addition to those shown and described herein, will be apparent to those skilled in the art from the foregoing description. Such modifications are also intended to fall within the scope of the appended claims.

Example 1

A lab scale runaway reaction test was conducted to assess ability of a stabilizer to quench the reaction. The test was conducted inside insulated Dewar flasks in order to conserve all the heat energy to the runaway reaction modeling a real event. The Dewar flasks do not have constriction, instead they have an open throat for venting. A commercially available peroxyacetic acid composition (peracetic acid 5 wt-%; acetic acid 5-10 wt-%; hydrogen peroxide 10-30 wt-%; remaining water) was used with iron to trigger a decomposition reaction as would occur with iron contaminants in a peroxide or peroxycarboxylic acid composition. The evaluated conditions are shown in Table 1. The 6 grams ferric chloride hexahydrate and ferric chloride anhydrous salt were added to 200 g of the peracetic acid/hydrogen peroxide composition in a 500 mL cylindrical Dewar flask and the temperature in the flasks were monitored over time. The ferric ions are a known antagonist for peroxide compounds as are chloride ions and both are likely responsible for the exothermic decomposition reaction that builds to an eventual literal boiling hot decomposition of both the peracetic acid and the hydrogen peroxide.

A limitation of the laboratory assessments described herein is that the iron chloride is an effective contaminant to initiate rapid and aggressive boil out in the peroxycarboxylic acid composition, however the chloride ion may actually interfere with the stabilizer used to quench the runaway reaction. The HEDP stabilizer for example is intended for metals and not chloride. However, the testing in the field or non-laboratory reactions overcome this limitation of the laboratory examples as they do not experience such exaggerated contamination conditions such as those described herein.

TABLE 1

| Sample | Mass, g $FeCl_3$, 45% | Mass, g $FeCl_3$, 100% | Mass, g Total $FeCl_3$ | ppm Total $FeCl_{3\ in\ peracid}$ | Mass of Peracid, g Peroxyacetic Acid | Quench Stabilizer | Quench Mass, g | wt % ratio Stabilizer |
|---|---|---|---|---|---|---|---|---|
| A | 6 | 0.5 | 3.2 | 16000 | 200 | none | 0 | NA |
| B | 6 | 0.25 | 2.95 | 14750 | 200 | none | 0 | NA |
| C | Rxn abandoned | | | | 200 | none | 0 | NA |
| D | 6 | 0.5 | 3.2 | 16000 | 200 | HEDP (60%) | 20 | 10 wt % |
| E | 6 | 0.5 | 3.2 | 16000 | 200 | DI-H2O | 20 | 10 wt % |
| F | 6 | 0.5 | 3.2 | 16000 | 200 | HEDP (60%) | 10 | 5 wt % |
| G | 6 | 0.5 | 3.2 | 16000 | 200 | HEDP (60%) | 5 | 2.5 wt % |
| G2 | 6 | 0.5 | 3.2 | 16000 | 200 | HEDP (60%) | 5 | 2.5 wt % |

Samples A and B were not treated with any stabilizer and demonstrate the runaway negative Controls. Sample C was discarded. Samples D, F, G, and G2 had the stabilizer HEDP added to the peroxyacetic acid composition. Sample E was run with equivalent water (to the stabilizer) as a positive Control: also confirming that the quench of the HEDP stabilizer Samples were not due to heat sink or simple dilution of the peroxyacetic acid composition with water.

Figure 4:
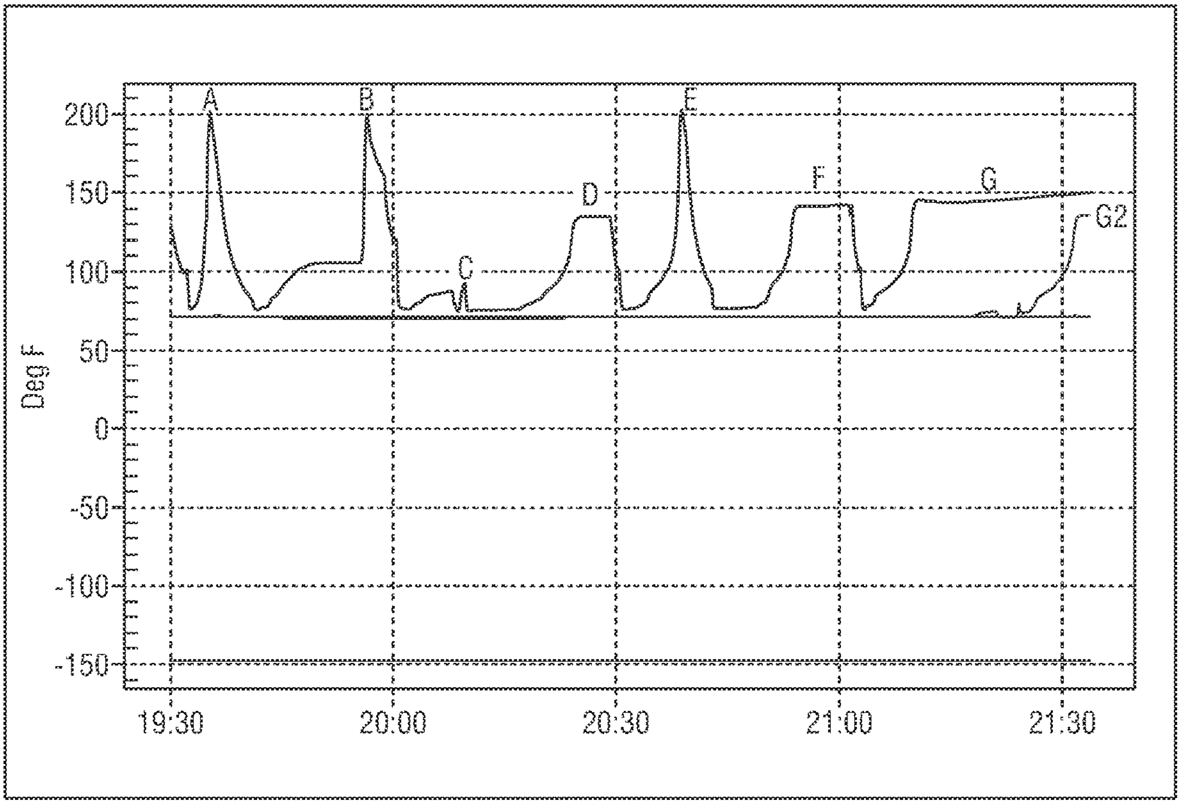
FIG. 4 shows a heat histogram measuring boil out reactions of lab scale iron-induced runaway decomposition tests of a peroxyacetic acid composition of several samples, including samples with added water or stabilizer to quench the reaction as described in Example 1.

The results are shown in FIG. 4, illustrating samples D, F, G, and G2 dosed with the HEDP stabilizer were able to quench the decomposition reaction. The x-axis of the figure shows the time of the measurements, and the y-axis shows the temperature in degrees Fahrenheit. Samples A and B show a runaway reaction, the temperatures quickly boil out to 200° F. where the chemistry boils off as a result of the contaminants decomposing the peroxycarboxylic acid composition and steam comes off the system which is a result of the oxygen liberated in the decomposition reaction and the consumption of the peroxygen species (here the peroxyacetic acid), leaving hot water in the flask. This reaction in the laboratory is an accelerated decomposition reaction to show a fast contamination and runaway over minutes instead of hours to days as would take place in larger volumes and less significant contamination.

The 2.5% relative mass (G samples) partially quenched but continued to climb. Both 5% and 10% (F and D respectively) performed well in that the reaction was quenched (or stated another way the exotherm was truncated) and no further increase in temperature was observed, confirming the quench of the runaway reaction. The data shows that the temperature in the flasks cools down relatively slowly which is a result of the shape of the flask container itself holding the peroxycarboxylic acid composition as well as the exaggerated contamination conditions.

This set of laboratory experiments shows that as little as a 2.5% ratio of quench solution in the form of HEDP (60% aq.) was capable of completely arresting the exothermic reaction. To demonstrate if this was simply a heat quenching effect, the HEDP solution was substituted by as much as 10% room temperature deionized water (E sample) which showed very slight effect on the progress of the eventual runaway (i.e. a slightly less steep curve to the boil out). As is stated in literature quenching these types of runaway reactions by simple thermal means may require as much as 400% relative water quenches. Since there are commercial interests in as large as 30,000-gallon tanks of peracids (e.g. peracetic acid solutions) it is imperative that the quench be as potent as possible. In some aspects this would be on the order of about 2.5% to about 10% of the target vessel.

Example 2

A large-scale quench test was also completed. Approximately 100,000 pounds of a peroxyacetic acid composition stored in approximately 37 storage totes, wherein each tote had a volume of 1000 L or around 330 gallons (i.e. standard Intermediate Bulk Containers (IBC)), that became contaminated with zinc were tested to confirm ability of the stabilizer HEDP to control a runaway decomposition reaction underway, as assessed by off gassing and self-heating of the peroxyacetic acid composition in the totes. The self-heating was a warm to hot increase in temperatures of the storage totes.

The tote that housed the composition with the runaway reaction had a temperature of at least 99.9° C. and the remainder of the heat energy was used to convert water to steam. The remaining totes were not able to obtain a temperature reading. They were warm to the touch and various qualitative assessments were made. For example, the material was visibly off gassing, and the totes were reported to have been bulging (i.e. exceeding the vent capacity) and there was a slight amount of vapor escaping.

HEDP stabilizer was delivered on site and added to each tote to provide a 10% target dosing of HEDP. Approximately 7% of the total volume of each tote of the HEDP was dosed/added to the contaminated product. Onsite assessment confirmed the HEDP was able to quench the reaction, stopped the off gassing, and allowed the containers to cool enough for them to be transported safely for disposal.

Example 3

Additional laboratory testing was conducted to evaluate an additional stabilizer. For practical purposes, the lab induced runaway described in this Example and Example 1 were scaled to cause complete destruction of the chemistries within 5-60 minutes, but these relatively high levels of contamination are generally in great excess to the contamination levels necessary to cause the runaways in large vessels, in some instances by a factor of 100-1000 higher. Forensic analysis of a 1000 L tote which ran away over a period of several days boiling out and spilling out its contents, it was found that only about 1 ppm copper along with sub ppm levels of several transition metals were all that was necessary to contaminate the chemistry and induce the runaway reaction. This demonstrates that a lower wt-% ratio of stabilizer to the chemistry would be effective to quench a reaction.

Figure 7:
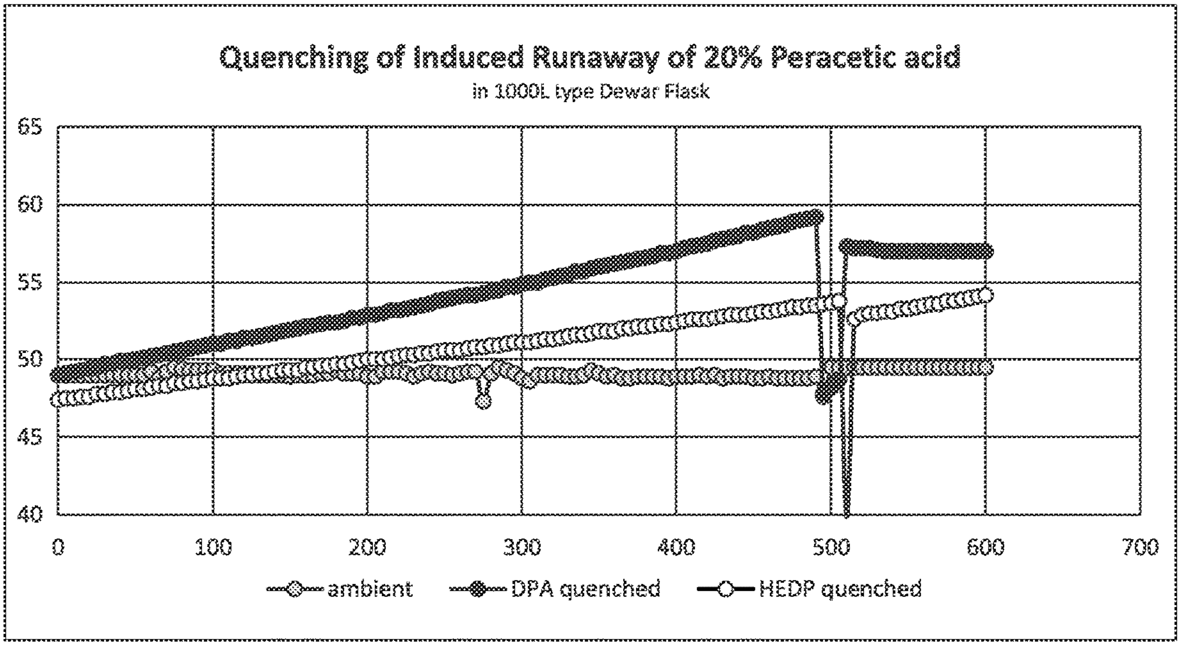
FIG. 7 is a graph showing temperature measurements of a lab scale iron-induced runaway decomposition reaction and the use of two different stabilizers to quench as described in Example 3.

FIG. 7 shows testing over a period of 600 minutes comparing HEDP to DPA. The testing with only 0.6 wt % HEDP stabilizer (9 g of 60% HEDP added to 900 g of the 20% peracid) failed to quench the runaway (as evidenced by the continued climb after returning the flask to the 48° C. oven). This is shown in FIG. 7 when the HEDP was dosed just after 500 minutes the exotherm was quenched, until the heating was resumed and the curve then continues to produce the exotherm and exhibit a slow runaway reaction. In contrast, the 0.1 wt % dipicolinic acid stabilizer (0.9 grams DPA added to 900 g of the 20% peracid) quenched it for at least 100 minutes (as evidenced by the isothermal condition and the slope decreasing to zero showing complete arrest sustained for 100 minutes (shown as 600 minutes in the graph)).

Example 4

In various applications it is desired to provide a combination of stabilizers to quench a reaction, such as both HEDP and DPA. In field applications of use a combination of stabilizers is preferred including a range of about 1:3 to 3:1, and preferably a 1:1 combination (or 50/50 mixture). As the dipicolinic acid is a powder of only several percent solubility in water in order to maximize solubility a mixture of the sodium or potassium salts of HEDP and dipicolinic acid is a preferred embodiment. Testing was conducted using the stabilizer IV shown in Table 2 and according to the conditions of Table 3.

TABLE 2

| Stabilizer components | I | II | III | IV |
|---|---|---|---|---|
| DPA (100%) | 100 | | | 9 |
| HEDP (60%) | | 100 | 17 | 9 |
| NaOH (100%) | | | 9 | 8 |
| Water | | | 74 | 84 |
| Physical form | Solid | Liquid | Liquid | Liquid |

Table 2 shows additional blends of stabilizer components that can be employed as described herein. The examples of stabilizers that could be provided as solids or liquids show exemplary single stabilizer formulations to dose to a runaway reaction as well as combination stabilizers. In some exemplary embodiments, the NaOH is added to neutralize the acidic HEDP protons and DPA protons. Conversion of the acids to the sodium salts via NaOH, provides enhanced water solubility especially for the combination of the two agents which have been previously shown to act synergistically towards stabilizing peracids.

TABLE 3

| Sample | Mass, g $FeCl_3$ * 6H2O | Mass, g Total $FeCl_3$, | ppm Total $FeCl_3$ in peracid | Mass of Peracid, g Peroxyacetic Acid (25% peracid/ 12% H2O2) | Quench Stabilizer | Quench Mass, g | Quench wt % ratio Stabilizer |
|---|---|---|---|---|---|---|---|
| A | 0.5 | 0.3 | 3000 | 100 | IV | 10 | 10 wt % |
| B | 0.5 | 0.3 | 3000 | 100 | IV | 20 | 20 wt % |
| C | 0.5 | 0.3 | 3000 | 100 | IV | 20 | 20 wt % |
| D | 0.5 | 0.3 | 3000 | 100 | IV | 40 | 40 wt % |

Figure 8:
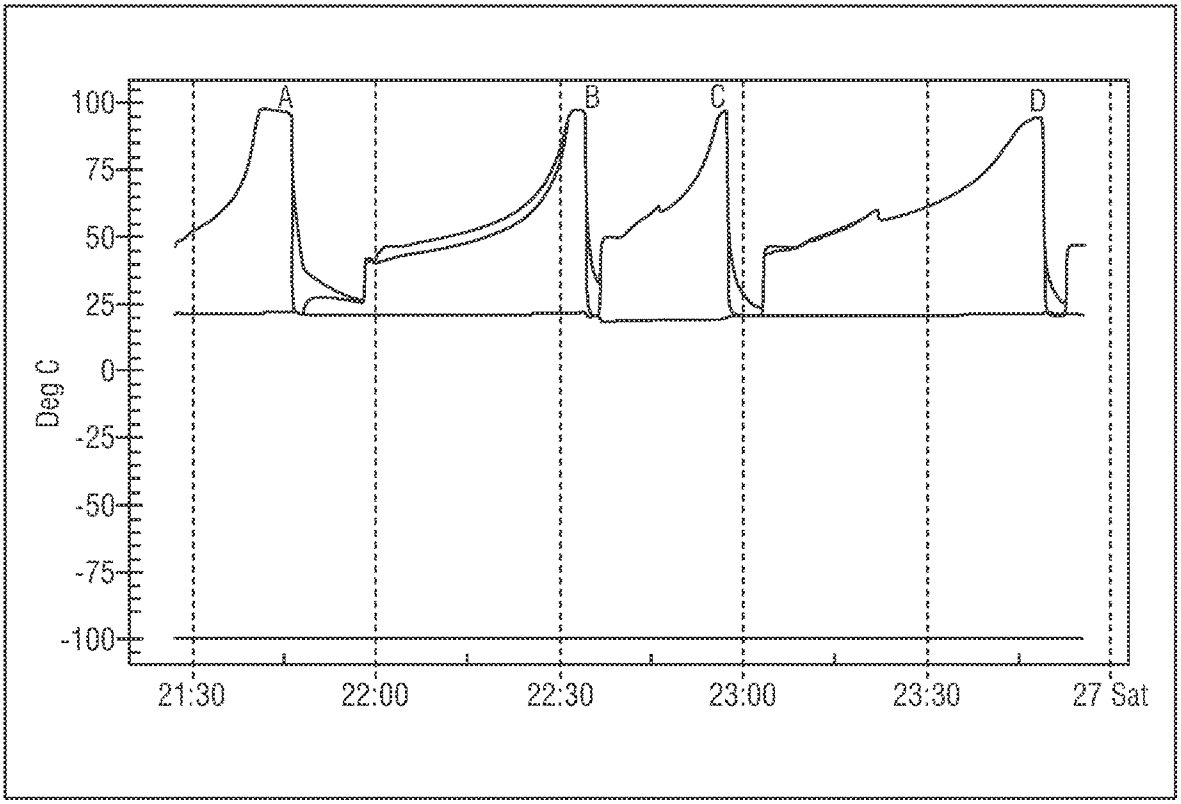
FIG. 8 is a heat histogram measuring boil out reactions of lab scale iron-induced runaway decomposition tests of a more concentrated peroxyacetic acid composition of several samples, including samples with added stabilizers to quench the reaction as described in Example 4.

Additional testing following the methods of Example 1 were conducted using a more concentrated peracid composition. In Example 1 a 5% peroxyacetic acid composition was evaluated and, in this testing, a 25% peroxyacetic acid composition with 11% hydrogen peroxide equilibrium mixture was evaluated. This condition represents a more potent chemistry for potential of a runaway reaction. In this reaction the preferred 50/50 blend of stabilizers was not as successful as the first example with the more dilute peroxyacid composition. This can be seen in FIG. 8 where the inflection in the curves around 50° C. when the stabilizers were added to quench the reactions, but they continued boiling off the chemistry at ~100° C. (at least of A-D in FIG. 8). The addition of the stabilizers show a significant slowing down of the reaction.

However, as mentioned in Example 1, this is not indicative of non-laboratory or actual use of the chemistries where the is not such excessive contamination of the systems and there is a much longer timeline (e.g. 2-3 days as opposed to minutes/hours) of the runaway reactions. The multiple evaluations confirm that the use of the systems and methods described herein are more readily quenched in the field than in the accelerated and exaggerated laboratory conditions using the much higher contaminant levels to induce the runaway reactions on a smaller scale (i.e. flask).

Example 5

Figure 9:
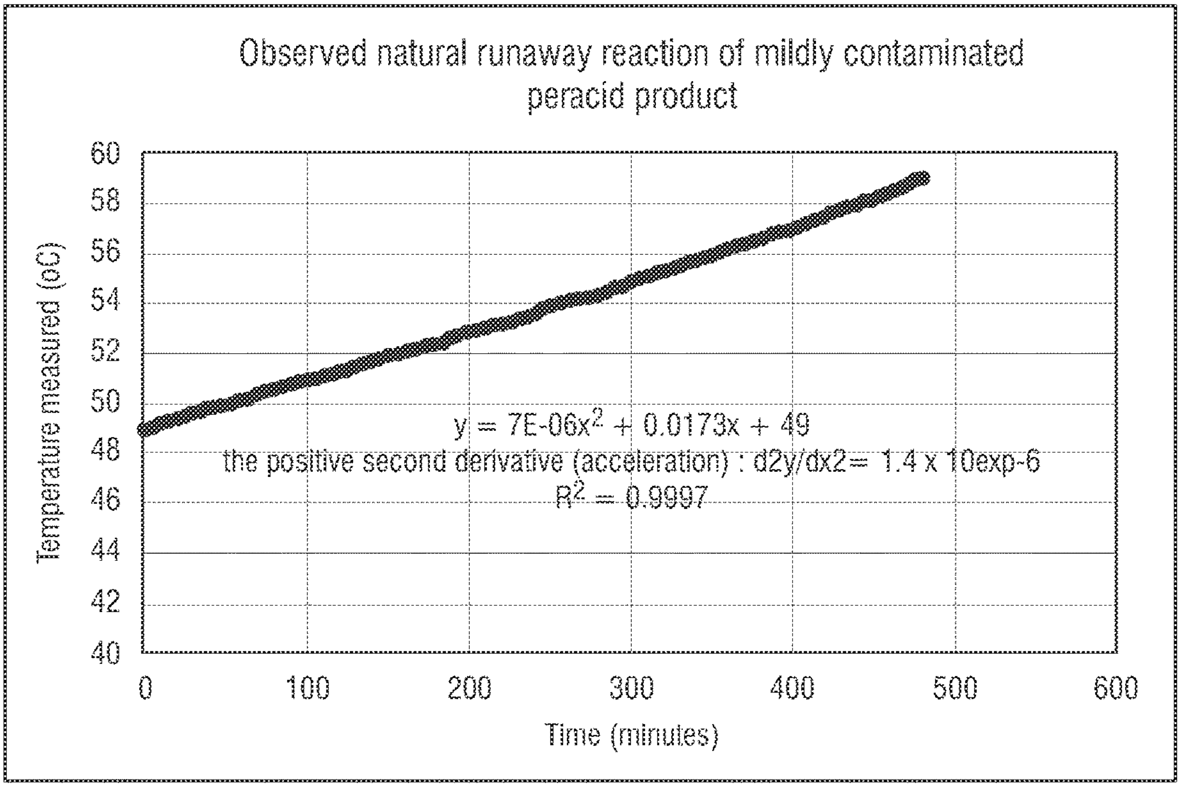
FIG. 9 is a graph showing temperature measurements and the positive second derivative (acceleration) of change in dTemp/dTime as described in Example 5.

A runaway reaction was observed to analyze the rate of temperature increase during the runaway reaction as measured in Table 4 and depicted in FIG. 9.

TABLE 4

| | | dTemp/dTime (rate of temp climb) | | | |
|---|---|---|---|---|---|
| Time (min) | Temp (° C.) | (oC/20 min) | (oC/ hour) | (oC/ 2 hour) | (oC/ 3 hour) |
| 20 | 49.4 | 0.4 | | | |
| 40 | 49.9 | 0.5 | | | |
| 60 | 50.2 | 0.3 | 1.2 | | |
| 80 | 50.6 | 0.4 | | | |
| 100 | 51 | 0.4 | | | |
| 120 | 51.4 | 0.4 | 1.2 | 2.4 | |
| 140 | 51.7 | 0.3 | | | |
| 160 | 52.1 | 0.4 | | | |
| 180 | 52.4 | 0.3 | 1 | | 3.4 |
| 200 | 52.9 | 0.5 | | | |
| 220 | 53.2 | 0.3 | | | |
| 240 | 53.6 | 0.4 | 1.2 | 2.2 | |
| 260 | 54.1 | 0.5 | | | |
| 280 | 54.4 | 0.3 | | | |
| 300 | 54.9 | 0.5 | 1.3 | | |
| 320 | 55.3 | 0.4 | | | |
| 340 | 55.7 | 0.4 | | | |
| 360 | 56.2 | 0.5 | 1.3 | 2.6 | 3.8 |
| 380 | 56.6 | 0.4 | | | |
| 400 | 57 | 0.4 | | | |
| 420 | 57.5 | 0.5 | 1.3 | | |
| 440 | 58 | 0.5 | | | |
| 460 | 58.5 | 0.5 | | | |
| 480 | 59 | 0.5 | 1.5 | 2.8 | |

In some embodiments, a change in dTemp/dTime measured in regular intervals (i.e. 20 minutes), can be monitored or processed, such as described in Example 3 with successive 20-minute intervals showing an increased rate value in order to trigger a quenching process. Since early intervention is critical, measuring dTemp/dTime is an efficient way to process data in an objective manner. As one skilled in the art could ascertain from the disclosure herein, a mildly contaminated system could have single measurements that could be interpreted as false indications of a runaway reaction. As shown with this data by the time 3 successive rate increases are measured the system is excessively hot and may not be quenchable. In this case if rate increases are measured in larger intervals such as 1 hour, 2 hour or 3 hours it allows some overcoming of the natural noise in the data, but not until one uses the 2-hour intervals are 3 successive rate increases found and by this time the system temperature is a 60° C.

Therefore, this study shows that an effective and efficient approach is to use all of the temp vs time data points to define a 2nd order polynomial or higher and assuming over 98% correlation a second derivative can be calculated, and one arrives at a very objective (i.e. yes or no) determination of a runaway reaction. If the second derivative is positive, there is a runaway reaction and requires quenching. Beneficially there is no need to lose critical hours before the intervention is triggered. A final safeguard is to use a simple maximum system temperature that can be predetermined, such as 60° C.

It is to be understood that while the invention has been described in conjunction with the detailed description thereof, the foregoing description is intended to illustrate, and not limit the scope of the invention, which is defined by the scope of the appended claims. Other embodiments, advantages, and modifications are within the scope of the following claims. In addition, the contents of all patent publications discussed supra are incorporated in their entirety by this reference.

The features disclosed in the foregoing description, or the following claims, or the accompanying drawings, expressed in their specific forms or in terms of a means for performing the disclosed function, or a method or process for attaining the disclosed result, as appropriate, may, separately, or in any combination of such features, be utilized for realizing the invention in diverse forms thereof.

What is claimed is:

1. A method of quenching a runaway reaction of a peroxide or peroxycarboxylic acid composition comprising:

detecting a predetermined increase in rate of temperature increase as a function of time, in a tank, wherein the tank contains a peroxycarboxylic acid composition or mixing a peroxycarboxylic acid-forming composition, wherein the peroxycarboxylic acid composition or mixing a peroxycarboxylic acid-forming composition comprises hydrogen peroxide and peroxycarboxylic acid;

dispensing from about 2 wt-% to about 10 wt-% based on the weight of the peroxycarboxylic acid composition or mixing a peroxycarboxylic acid-forming composition of a stabilizer consisting of phosphoric acid or salt thereof, a pyrophosphoric acid or salt thereof, a phosphonic acid or salt thereof, or a combination thereof into the tank, wherein the stabilizer is combined with a dye to provide a visual indicator of the quenching; and quenching the runaway reaction wherein at least about 80% of the peroxy species in the peroxycarboxylic acid composition or peroxycarboxylic acid-forming composition in the tank is salvaged after the quenching the runaway reaction and can be reused instead of disposed.

2. The method of claim 1, wherein the stabilizer is added within about 15 seconds of the detecting of the increase in rate of temperature increase.

3. The method of claim 1, wherein the stabilizer is 1-hydroxyethylidene-1,1-diphosphonic acid (HEDP) or a salt thereof.

4. The method of claim 1, wherein the stabilizer is a liquid, solid, or a powder.

5. The method of claim 1, wherein the stabilizer is dosed at a rate of about 2.5 wt-% to about 5 wt-% based on the weight of the peroxycarboxylic acid composition or peroxycarboxylic acid-forming composition in the tank.

6. The method of claim 1, wherein at least about 90% of the peroxy species in the peroxycarboxylic acid composition or peroxycarboxylic acid-forming composition is salvaged after the quenching the runaway reaction and can be reused instead of disposed.

7. The method of claim 1, wherein at least about 95% of the peroxy species in the peroxycarboxylic acid composition or peroxycarboxylic acid-forming composition in the tank is salvaged after the quenching the runaway reaction and can be reused instead of disposed.

* * * * *